(12) United States Patent
Ye

(10) Patent No.: US 9,895,344 B2
(45) Date of Patent: Feb. 20, 2018

(54) TREATING VARIOUS DISORDERS WITH 7,8-DIHYDROXYFLAVONE AND DERIVATIVES THEREOF

(75) Inventor: Keqiang Ye, Lilburn, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 618 days.

(21) Appl. No.: 13/055,861

(22) PCT Filed: Jul. 23, 2009

(86) PCT No.: PCT/US2009/051535
§ 371 (c)(1),
(2), (4) Date: Feb. 23, 2011

(87) PCT Pub. No.: WO2010/011836
PCT Pub. Date: Jan. 28, 2010

(65) Prior Publication Data
US 2011/0144196 A1 Jun. 16, 2011

Related U.S. Application Data

(60) Provisional application No. 61/118,910, filed on Dec. 1, 2008, provisional application No. 61/089,260, filed on Aug. 15, 2008, provisional application No. 61/083,658, filed on Jul. 25, 2008.

(51) Int. Cl.
A01N 43/16 (2006.01)
A61K 31/35 (2006.01)
A61K 31/353 (2006.01)

(52) U.S. Cl.
CPC .................. A61K 31/353 (2013.01)

(58) Field of Classification Search
CPC .................................... A61K 31/353
USPC ....................................... 514/456
See application file for complete search history.

(56) References Cited

U.S. PATENT DOCUMENTS

| | | | |
|---|---|---|---|
| 2002/0198248 A1* | 12/2002 | Kelly et al. | 514/400 |
| 2004/0198750 A1 | 10/2004 | Green | |
| 2006/0025337 A1 | 2/2006 | Sinclair | |
| 2006/0111435 A1 | 5/2006 | Sinclair | |

FOREIGN PATENT DOCUMENTS

| | | |
|---|---|---|
| JP | XP-002652725 | 7/2008 |
| WO | WO 9505169 A1 * | 2/1995 |
| WO | WO 2004/037193 | 6/2004 |
| WO | WO1995005169 | 2/2005 |
| WO | WO2006079021 | 7/2006 |
| WO | WO2008008033 | 1/2008 |
| WO | WO 2008/091710 | 7/2008 |

OTHER PUBLICATIONS

Anjaneyulu et al. "Antidepressant activity of quercetin, a bioflavonoid, in streptozotocin-induced diabetic mice." Journal of medicinal food 6.4 (2003): 391-395.*
Wach et al. ("Quercetin content in some food and herbal samples." Food Chemistry 100.2 (2007): 699-704).*
Nabavi et al. (Review Neuroprotective effects of chrysin: From chemistry to medicine. Neurochemistry International vol. 90, Nov. 2015, pp. 224-231).*
Jang et al., A selective TrkB agonist with potent neurotrophic activities by 7,8-dihydroxyflavone. Proc Natl Acad Sci U S A. Feb. 9, 2010;107(6):2687-92.
Jang et al., A selective TrkB agonist with potent neurotrophic activities by 7,8-dihydroxyflavone. Proc Nati Acad Sci U S A. 2010,107(6):2687-92.
Jang et al., A selective TrkB agonist with potent neurotrophic activities by 7,8-dihydroxyflavone. Proc Natl Acad Sci U S A. 2010,107(6):2687-92.
Anjaneyulu et al. Antidepressant Activity of Quercetin, a Bioflavonoid, in Streptozotocin-Induced Diabetic Mice, J Med Food 6 (4) 2003, 391-395.
Devi, 7,8-Dihydroxyflavone, a Small-Molecule TrkB Agonist, Reverses Memory Deficits and BACE1 Elevation in a Mouse Model of Alzheimer's Disease, Neuropsychopharmacology (2012) 37, 434-444.
Jiang et al., Small molecule TrkB receptor agonists improve motor function and extend survival in a mouse model of Huntington's disease, Hum Mol Genet 2013, 22(12):2462-70.
Filho et al. Chronic Unpredictable Mild Stress Decreases BDNF and NGF Levels and Na+,K+-Atpase Activity in the Hippocampus and Prefrontal Cortex of Mice: Antidepressant Effect of Chrysin, Neuroscience, 289 (2015) 367-380.
Liu et al.,A Synthetic 7,8-Dihydroxyflavone Derivative Promotes Neurogenesis and Exhibits Potent Antidepressant Effect, J. Med. Chem., 2010, 53 (23), pp. 8274-8286.
European Search Report; Application No. EP 09 80 1005 dated Aug. 4, 2011.
AFD CHINA IP: Treating various disorder with 7, 8-dihydroxyflavone and derivatives thereof.

* cited by examiner

Primary Examiner — Layla Soroush
(74) Attorney, Agent, or Firm — Emory Patent Group

(57) ABSTRACT

Novel compounds and methods related to the activation of the TrkB receptor are provided. The methods include administering in vivo or in vitro a therapeutically effective amount of 7,8-dihydroxyflavone or derivative thereof. Specifically, methods and compounds for the treatment of disorders including neurologic disorders, neuropsychiatric disorders, and metabolic disorders (e.g., obesity) are provided. For example, a first method is provided of treating or reducing the risk of depression, anxiety, or obesity in a subject, which includes selecting a subject with or at risk of developing depression, anxiety, or obesity, and administering to the subject a therapeutically effective amount of 7,8-dihydroxyflavone or a derivative thereof. A further method of promoting neuroprotection in a subject also is provided, which includes selecting a subject in need of neuroprotection, and administering to the subject a therapeutically effective amount of 7,8-dihydroxyflavone or a derivative thereof.

3 Claims, 25 Drawing Sheets

Forced Swimming Test
Chronical Drug Treatment

TREATING VARIOUS DISORDERS WITH 7,8-DIHYDROXYFLAVONE AND DERIVATIVES THEREOF

This application claims the benefit of U.S. Provisional Applications No. 61/083,658, filed Jul. 25, 2008; 61/089,260, filed Aug. 15, 2008; and 61/118,910, filed Dec. 1, 2008. The entire disclosure of the prior applications is hereby incorporated by reference.

This invention was made with government support under Grant No. R01-NS045627 from the National Institutes of Health. The government has certain rights in this invention.

BACKGROUND

Neurologic and neuropsychiatric disorders such as depression, anxiety, amyotrophic lateral sclerosis, and central nervous system injuries, to name a few, afflict millions of people every year resulting in a multitude of symptoms including weight change, decreased energy, headaches, digestive problems, chronic pain, paralysis, and in certain instances, death.

One class of growth factors proposed as a treatment for neurologic and neuropsychiatric disorders are neurotrophins, which include brain-derived neurotrophic factor (BDNF). BDNF is believed to have neurotrophic action on various neuronal populations including sensory neurons, motor neurons, dopaminergic neurons of the substantia nigra, and cholinergic neurons of the basal forebrain, which are involved in several neurologic and neuropsychiatric disorders. Preclinical evidence indicates that BDNF might be useful as a therapeutic agent for various neurologic and neuropsychiatric disorders; however, the in vivo instability of such a peptide therapy limits its usefulness.

Neurotrophins are also indicated in metabolic disorders. Mutations in the tyrosine kinase receptor trkB or in one of its natural ligands, e.g., BDNF or neurotrophin-4 (NT4), are known to lead to severe hyperphagia and obesity in rodents and humans. Administration of trkB ligands such as BDNF or NT4 have been shown to suppress appetite and body weight in a dose-dependent manner in several murine models of obesity. Accumulating evidence indicates that TrkB signaling directly modulates appetite, metabolism, and taste preference. TrkB agonists thus emerge as potential therapeutics for metabolic disorders.

SUMMARY

Novel compounds and methods for the treatment of disorders including neurologic disorders, neuropsychiatric disorders (e.g., anxiety or depression), and metabolic disorders (e.g., obesity) are provided. The methods include administering to a subject a therapeutically effective amount of 7,8-dihydroxyflavone or derivative thereof. For example, a first method is provided related to treating or reducing the risk of depression, anxiety, or obesity in a subject, which includes selecting a subject with or at risk of developing depression, anxiety, or obesity, and administering to the subject a therapeutically effective amount of 7,8-dihydroxyflavone or a derivative thereof. A further method of promoting neuroprotection in a subject is provided, which includes selecting a subject in need of neuroprotection, and administering to the subject a therapeutically effective amount of 7,8-dihydroxyflavone or a derivative thereof.

A method of activating a TrkB receptor on a neuron also is provided. The method includes providing the neuron with a TrkB receptor, then contacting the TrkB receptor in vitro with a 7,8-dihydroxyflavone or derivative thereof in an amount sufficient to activate the TrkB receptor. The neuron can be, for example, a mammalian cell.

Compounds are also provided that can be used in the methods described herein. These compound are of the following formula:

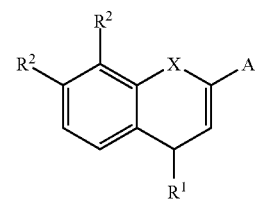

or a pharmaceutically acceptable salt or prodrug thereof. In this compound, X is $CH_2$, $NR^3$, O, or S, wherein $R^3$ is selected from hydrogen, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl; $R^1$ hydrogen, —OH, =O, or —$NR^4R^5$, wherein $R^4$ and $R^5$ are each independently $R^3$, substituted or unsubstituted $C_{3-12}$ cycloalkyl, substituted or unsubstituted $C_{3-12}$ heterocycloalkyl, substituted or unsubstituted $C_{3-12}$ cycloalkenyl, substituted or unsubstituted $C_{3-12}$ heterocycloalkenyl, substituted or unsubstituted $C_{3-12}$ cycloalkynyl, or substituted or unsubstituted $C_{3-12}$ heterocycloalkynyl; $R^2$ is —$OR^6$ or —$NR^6R^7$, wherein $R^6$ and $R^7$ are each independently $R^4$, —(C=O)$R^3$, or —(C=O)$OR^3$; and A is meta or para substituted phenyl or substituted or unsubstituted $C_5$ or $C_6$ heteroaryl, wherein $R^1$ is other than =O, one of $R^2$ is other than hydroxyl, or A is other than an unsubstituted phenyl.

The details of one or more examples of the compounds and methods are set forth in the accompanying drawings and the description below. Other features, objects, and advantages will be apparent from the description and drawings, and from the claims.

DETAILED DESCRIPTION

Figure 1A:
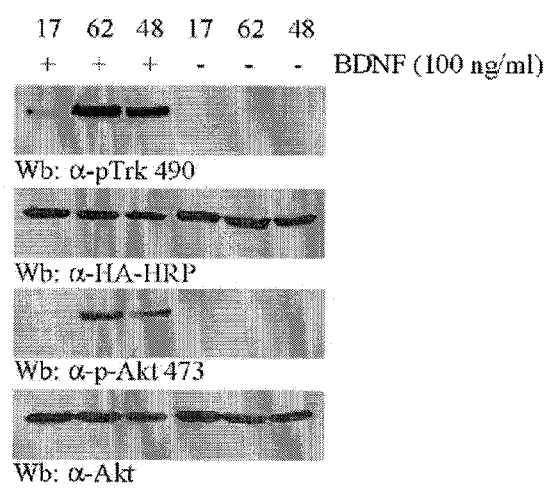
FIG. 1A shows a Western blot demonstrating phosphorylation of Trk490 and Akt in cell lines stably transfected with TrkB.

Described herein are compounds and methods for the activation of the TrkB receptor. These compounds and methods are effective in the treatment of disorders associated with activation of the TrkB receptor including neurological disorders, neuropsychiatric disorders, and metabolic disorders. Examples of neurological and neuropsychiatric disorders include depression, anxiety, Alzheimer's, CNS injuries, and the like. Examples of metabolic disorders include obesity and hyperphagia. Specifically, provided herein, are the compound 7,8-dihydroxyflavone and pharmaceutically acceptable salts, prodrugs, and derivatives thereof. Methods of their use in the treatment of neurologic disorders, neuropsychiatric disorders, and obesity are also described herein.

The compound 7,8-dihydroxyflavone is represented by Compound I:

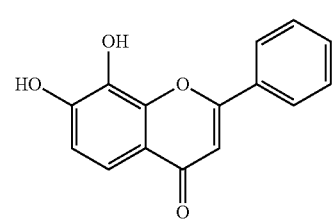

Derivatives of 7,8-dihydroxyflavone useful with the methods described herein include compounds represented by Compound II:

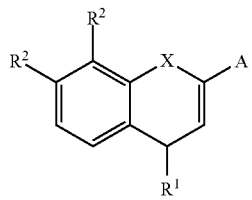

II and pharmaceutically acceptable salts and prodrugs thereof. The compounds represented by Compound II include, for example, derivatives of 7,8-dihydroxyflavone that are more soluble than 7,8-dihydroxyflavone and retain the ability to activate the TrkB receptor. The effectiveness of various derivatives relative to 7,8-dihydroxyflavone with respect to activating the TrkB receptor may vary. However, without wishing to be bound by theory, even if a particular derivative has a lower effectiveness than 7,8-dihydroxyflavone at activating the TrkB receptor, improvements in solubility may increase the overall effectiveness of the derivative as used, e.g., in the methods described herein.

In Compound II, X is $CH_2$, $NR^3$, O, or S, wherein $R^3$ is selected from hydrogen, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl.

Also in Compound II, $R^1$ is hydrogen, —OH, =O, or —$NR^4R^5$, wherein $R^4$ and $R^5$ are each independently $R^3$, substituted or unsubstituted $C_{3-12}$ cycloalkyl, substituted or unsubstituted $C_{3-12}$ heterocycloalkyl, substituted or unsubstituted $C_{3-12}$ cycloalkenyl, substituted or unsubstituted $C_{3-12}$ heterocycloalkenyl, substituted or unsubstituted $C_{3-12}$ cycloalkynyl, or substituted or unsubstituted $C_{3-12}$ heterocycloalkynyl. Examples of $R^1$ include —$NH_2$, —$NHCH_3$, —$N(CH_3)_2$,

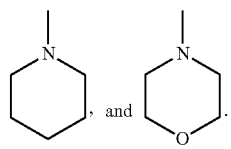

and.

Additionally, in Compound II, $R^2$ is —$OR^6$ or —$NR^6R^7$, wherein $R^6$ and $R^7$ are each independently $R^3$, —(C=O)$R^3$, or —(C=O)$OR^3$. One of $R^2$ is, for example,

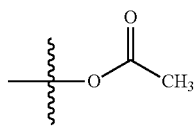 [SMILES: *OC(C)=O]

Further, in Compound II, A is meta or para substituted phenyl or substituted or unsubstituted $C_5$ or $C_6$ heteroaryl. For example, A is

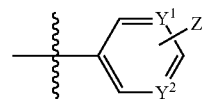

wherein $Y^1$ and $Y^2$ are each independently O, N, S, or $CH_2$; and Z is hydrogen, halogen, —$OR^4$, or —$NR^5R^6$. For further example, A is

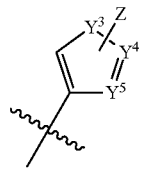

wherein $Y^3$, $Y^4$, and $Y^5$ are each independently O, N, S, or $CH_2$; and Z is hydrogen, halogen, —$OR^4$, or —$NR^5R^6$. Further examples of A include:

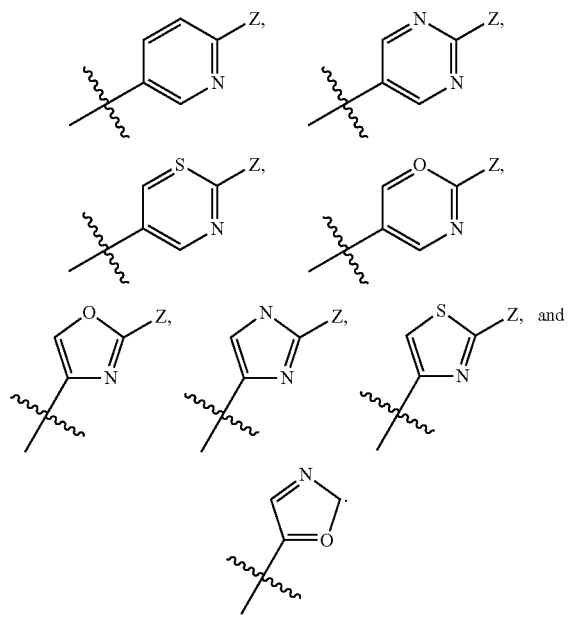

In Compound II, $R^1$ is other than =O, one of $R^2$ is other than hydroxyl, or A is other than an unsubstituted phenyl.

Specific examples of Compound II are as follows:

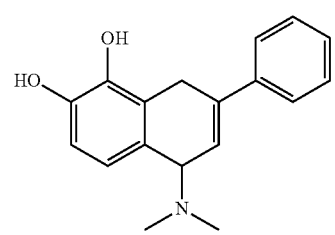

II-1

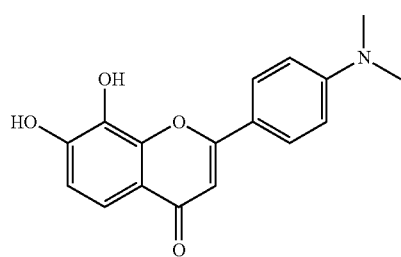 II-2
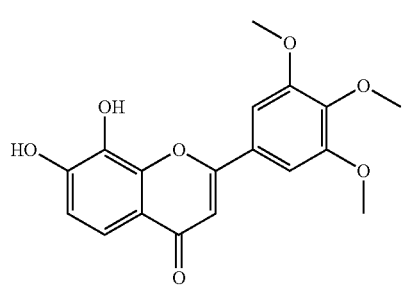 II-3
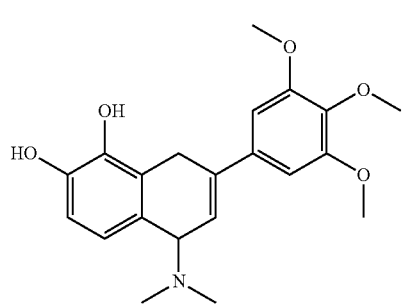 II-4
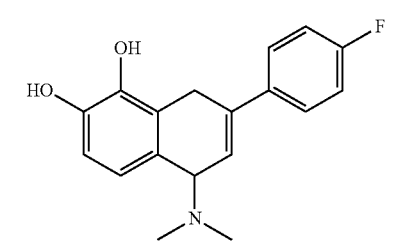 II-5
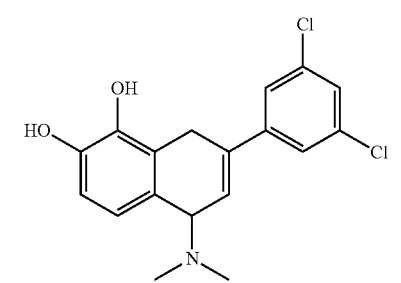 II-6
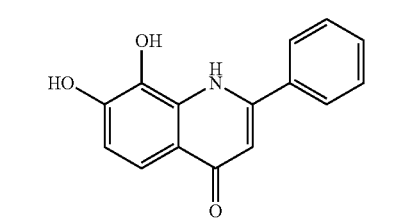 II-7
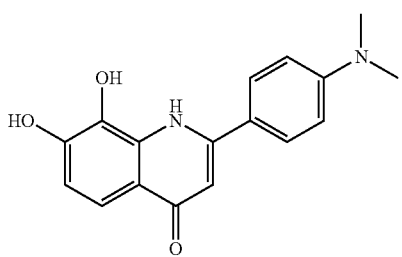 II-8
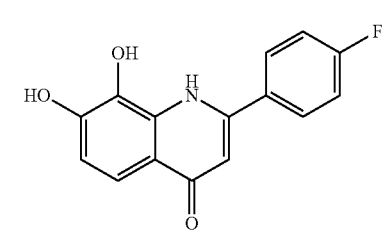 II-9
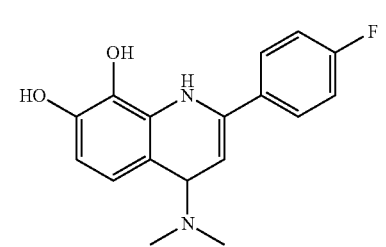 II-10
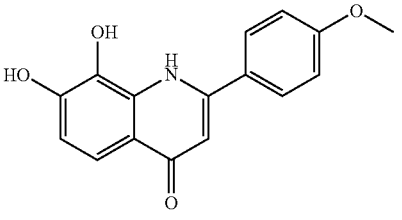 II-11
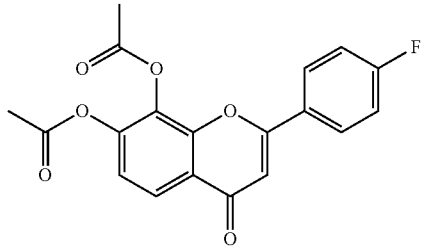 II-12
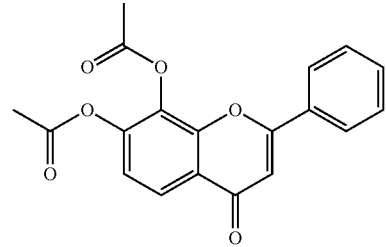 II-13

-continued

II-14
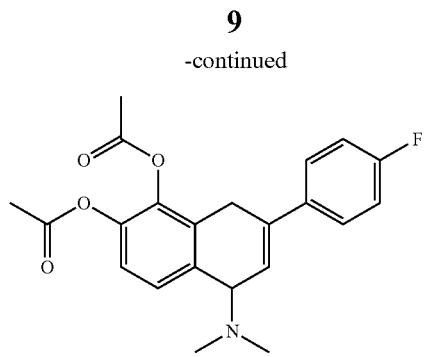

II-15
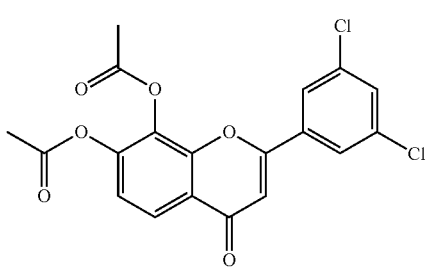

II-16
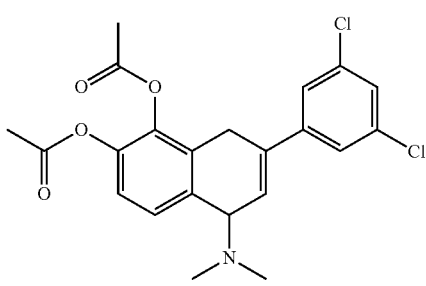

II-17
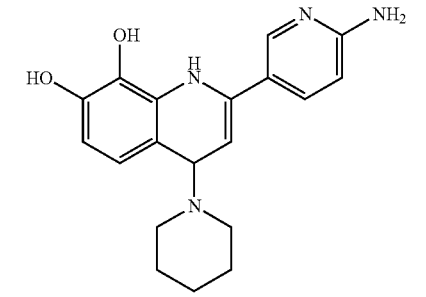

II-18
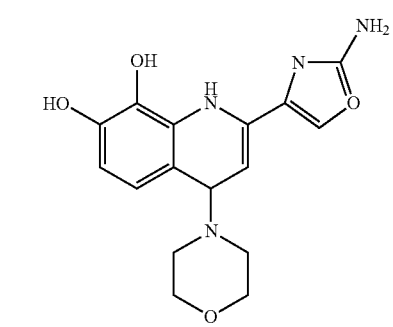

-continued

II-19
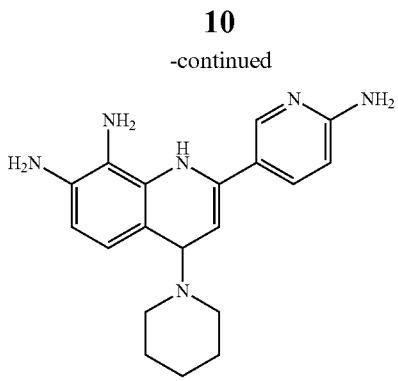

II-20
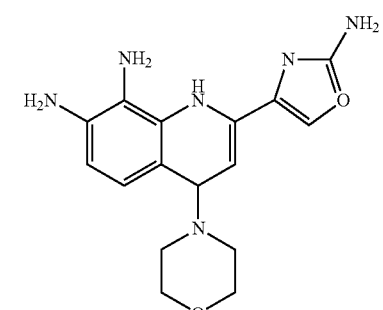

II-21
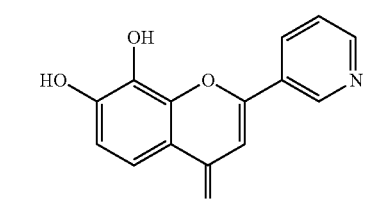

II-22
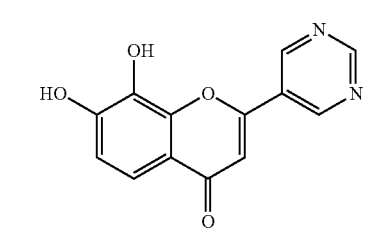

The compounds described herein can be prepared in a variety of ways known to one skilled in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Compound II include the addition, subtraction, or movement of the various constituents as described for each compound. Similarly, when one or more chiral centers is present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety. The synthesis and subsequent testing of various compounds as described for Compound II to determine efficacy is contemplated.

As used herein, the terms alkyl, alkenyl, and alkynyl include straight- and branched-chain monovalent substituents. Examples include methyl, ethyl, isobutyl, 3-butynyl, and the like. Heteroalkyl, heteroalkenyl, and heteroalkynyl are similarly defined but may contain O, S, or N heteroatoms or combinations thereof within the backbone. The term substituted indicates the main substituent has attached to it one or more additional components, such as, for example, OH, halogen, or one of the substituents listed above.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Examples of compounds described by Compound II and pharmaceutically acceptable salts and prodrugs thereof can be made, for example, using the method shown in Scheme 1.

Scheme 1

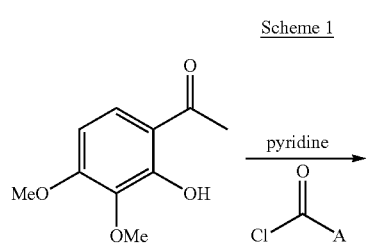

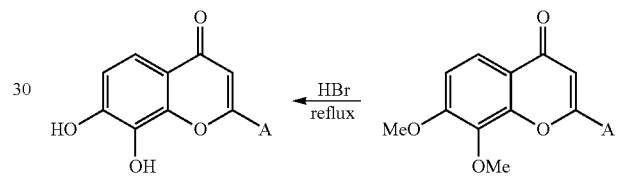

Additional examples of compounds described by Compound II and pharmaceutically acceptable salts and prodrugs thereof can be made, for example, using the method shown in Scheme 2.

Scheme 2

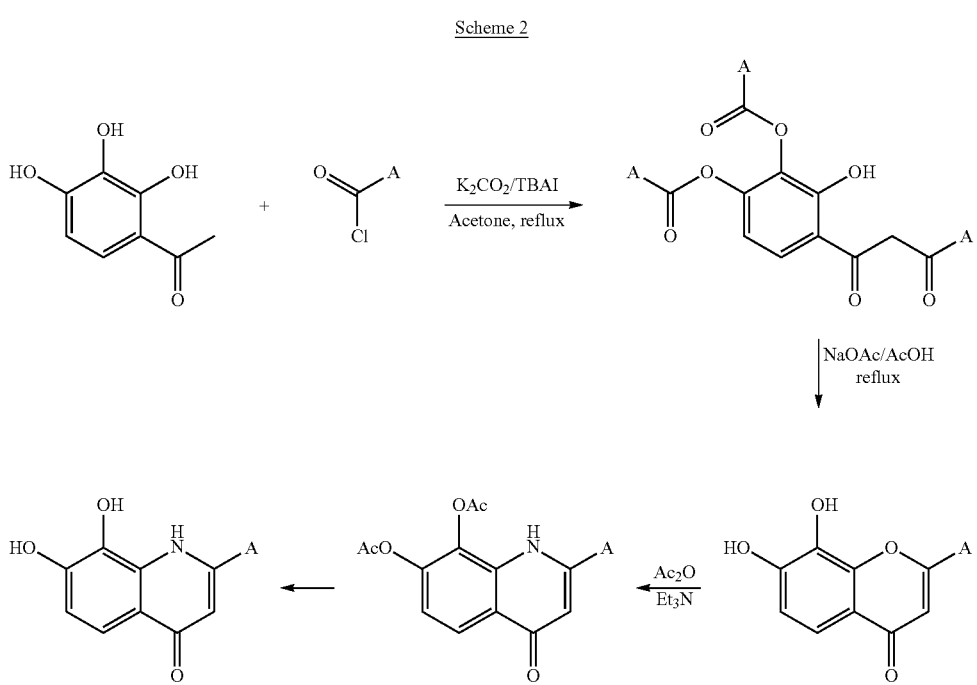

The methods described herein include a method of treating or reducing the risk of disorders associated with activation of the TrkB receptor including neurological disorders, neuropsychiatric disorders, and metabolic disorders in a subject. Examples of neurological and neuropsychiatric disorders include depression, anxiety, Alzheimer's, CNS injuries, and the like. Examples of metabolic disorders include obesity and hyperphagia. This method includes the steps of selecting a subject with or at risk of developing the neurological disorder, neuropsychiatric disorder, or obesity, and administering to the subject a therapeutically effective amount of 7,8-dihydroxyflavone or a derivative thereof. The 7,8-dihydroxflavone or derivative thereof can be administered systemically (e.g., orally, parenterally (e.g. intravenously), intramuscularly, intraperitoneally, transdermally (e.g., by a patch), extracorporeally, topically, by inhalation, subcutaneously or the like), by administration into the central nervous system (e.g., into the brain (intracerebrally or intraventricularly), spinal cord, or into the cerebrospinal fluid), or any combination thereof.

Also provided is a method of promoting neuroprotection in a subject. This method includes the steps of selecting a subject in need of neuroprotection, and administering to the subject a therapeutically effective amount of 7,8-dihydroxyflavone or derivative thereof. A subject in need of neuroprotection can, for example, be a subject that has amyotrophic lateral sclerosis (ALS) or a central nervous system injury. A central nervous system injury includes, for example, a brain injury, a spinal cord injury, or a cerebrovascular event (e.g., a stroke).

Methods can further comprise testing the effectiveness of 7,8-dihydroxyflavone or derivative thereof. Testing the effectiveness can include, but is not limited to, imaging (e.g., Magnetic Resonance Imaging (MRI)) and functional measurements (e.g., survival or clinical symptoms like analysis of speech patterns, logic, comprehension, memory, mood, and orientation). The method optimally further comprises adjusting the dosage or treatment regimen of 7,8-dihydroxyflavone or derivative thereof.

Further provided is a method of activating a TrkB receptor on a neuron (e.g., a mammalian neuron). This method includes the steps of providing a neuron with a TrkB receptor, and contacting the TrkB receptor in vitro with a 7,8-dihydroxyflavone or derivative thereof in an amount sufficient to activate the TrkB receptor. Also provided is a method of screening for an agent that potentiates the TrkB receptor activation. The screening method includes activating the TrkB receptor on a neuron as described and contacting the neuron with the agent to be screened. An enhanced effect indicates the agent potentiates the effect of 7,8-dihydroxyflavone or derivative thereof.

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are preferably suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The term pharmaceutically acceptable salt as used herein refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught herein.)

The compounds described above or derivatives thereof are useful in treating disorders associated with activation of the TrkB receptor including neurological disorders, neuropsychiatric disorders, and metabolic disorders (e.g., obesity), as well as for promoting neuroprotection in humans, e.g., including pediatric and geriatric populations, and animals, e.g., veterinary applications. A subject in need of neuroprotection is a subject at risk for or having a neurologic or neuropsychiatric disorder. Neurologic or neuropsychiatric disorders include, for example, depression, anxiety, amyotrophic later sclerosis, Alzheimer's disease, Huntington's disease, Rett syndrome, epilepsy, Parkinson's disease, dementia, diabetic neuropathy, peripheral neuropathy, and central nervous system injuries. Central nervous system injuries include, for example, spinal cord injury, stroke, hypoxia, ischemia, and brain injury. As used herein the terms promoting, treating, and treatment includes prevention; delay in onset; diminution, eradication, or delay in exacerbation of one or more signs or symptoms after onset; and prevention of relapse.

The methods and compounds as described herein are useful for both prophylactic and therapeutic treatment. For prophylactic use, a therapeutically effective amount of the compounds described herein or derivatives thereof are administered to a subject prior to onset (e.g., before obvious signs of neurologic or neuropsychiatric disorder), during early onset (e.g., upon initial signs and symptoms of neurological disorder), or an established neurological disorder. Prophylactic administration can occur for several days to years prior to the manifestation of symptoms of a disorder, e.g., a neurological or a neuropsychiatric disorder. Prophylactic administration can be used, for example, in the preventative treatment of subjects diagnosed with genetic neurological disorders such as Huntington's disease or prior to surgery in which stroke and hypoxia is a risk. Therapeutic treatment involves administering to a subject a therapeutically effective amount of the compounds described herein or derivatives thereof after a disorder, e.g., a neurological disorder, neuropsychiatric disorder, or metabolic disorder (e.g., obesity), is diagnosed.

Administration of compounds described herein or derivatives thereof can be carried out using therapeutically effective amounts of the compounds described herein or derivatives thereof for periods of time effective to treat a disorder. The effective amount of the compounds described herein or derivatives thereof may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

In these methods, the disorder being treated, e.g., depression, anxiety, central nervous system injury, metabolic disorder (e.g., obesity), or other disorder, can be further treated with one or more additional agents. The one or more additional agents and the compounds described herein or derivatives thereof can be administered in any order, including simultaneous administration, as well as temporally spaced order of up to several days apart. The methods may also include more than a single administration of the one or more additional agents and/or the compounds described herein or derivatives thereof. The administration of the one or more additional agents and the compounds described herein or derivatives thereof may be by the same or different routes and concurrently or sequentially. When treating with one or more additional agents, the 7,8-dihydroxyflavone or derivative thereof can be combined into a pharmaceutical composition with the one or more additional agents. For example, a 7,8-dihydroxyflavone or derivative thereof can be combined into a pharmaceutical composition with an anti-depressant, such as, for example imipramine, fluoxetine, paroxetine, and/or sertraline. As a further example, a 7,8-dihydroxyflavone or derivative thereof can be combined into a pharmaceutical composition with an anti-anxiolytic, such as, for example diazepam, alprazolam, clonazepam, and/or hydroxyzine.

The examples below are intended to further illustrate certain aspects of the methods and compounds described herein, and are not intended to limit the scope of the claims.

EXAMPLES

General Methods
Cells, Reagents and Mice

The human neuroblastoma SH-SY5Y and human embryonic kidney HEK293 cell lines were grown in DMEM with 10% fetal bovine serum (FBS) and 100 units penicillin-streptomycin at 37° C. with 5% $CO_2$ atmosphere in a humidified incubator. Mouse septal neuron x neuroblastoma hybrids SN56 cells were created by fusing N18TG2 neuroblastoma cells with murine (strain C57BL/6) neurons from postnatal 21 days septa. SN56 cells were maintained at 37° C. with 5% $CO_2$ atmosphere in DMEM medium containing 1 mM pyruvate and 10% FBS. T48 and T62 cells, stably transfected with rat TrkB, were cultured in the same medium containing 300 µg/ml G418.

Nerve growth factor (NGF) and brain-derived neurotrophic factor (BDNF) were from Roche; Basel, Switzerland. Phospho-Akt-473 and -308, Akt, and lamin A/C antibodies and Anti-TrkA were from Cell Signaling; Danvers, Mass. Anti-phospho-Erk1/2, anti-phospho-TrkA Y490, and anti-phospho-Akt 473 antibodies were from Upstate Biotechnology, Inc.; Billerica, Mass. Anti-TrkB antibody was from Biovision; Mountain View, Calif. Anti-p-TrkB 817 was from Epitomics, Inc. (Burlingame, Calif.). Anti-p-TrkA Y794 and anti-p-TrkB Y816 antibodies were previously described (Arevalo et al., Mol. Cell. Biol. 20: 5908-16, 2000; Rajagopal et al., J. Neurosci., 24:6650-8, 2004, which are incorporated herein and in their entirety at least with respect to these antibodies). The chemical library containing 2000 biologically active compounds was from The Spectrum Collection (MicroSource Discovery System, Inc.; Gaylordsville, Conn. 06755). 7,8-dihydroxyflavone was purchased from TCI America (Portland, Oreg.). All chemicals in the examples not indicated to have other sources were purchased from Sigma.

TrkB$^{F616A}$ mice (Chen X, et al., Neuron 46(1):13-21, 2005) and wild-type C57BL/6 mice were bred in a pathogen-free environment in accordance with Emory Medical School guidelines.

Primary Rat Cortical Neuron Culture

Primary cultured rat cortical neurons were prepared as follows. E17 rat pups were decapitated and cortex was extirpated, cross chopped, and suspended by pipetting for separation in 5% fetal calf serum (FCS), 5% horse serum (HS) DMEM. The cell suspension was then centrifuged at 250×g for 5 minutes. This operation was repeated again. Cells were seeded into polyethyleneimine-coated 10 $cm^2$ dishes and 12-well plates including coated-coverslips and incubated at 37° C. in 5% $CO_2$/95% air. After 3 hours, the culture medium was changed to Neurobasal containing B-27 supplement (Invitrogen; Carlsbad, Calif.) and incubated for 4 days. For maintenance, half of the culture medium was changed to fresh Neurobasal/B27 every 4 days. After 1 week, the dished cultured neurons were ready for use.

Immunofluorescent Staining

Primary hippocampal neurons were seeded on poly-L lysine coated coverslips in a 12-well plate. After 7 days in vitro, the neurons were treated with 100 ng/ml BDNF or variety of flavone compounds (1 µM) for 30 minutes, and then washed with PBS. Cells were fixed with 3% formaldehyde in PBS at room temperature for 10 minutes. The cells were then permeabilized and blocked by 0.4% Triton X-100 and 2% FBS in PBS at room temperature for 15 minutes, washed with PBS three times and treated with anti-MAP2 (1:200) and anti-phospho-TrkB antibodies (1:500). After staining with FITC- or Rhodamine-conjugated secondary antibody, the coverslips were mounted on slides. Fluorescent images were taken by OLYMPUS IX71 fluorescence microscope (Olympus; Center Valley, Pa.).

Immunohistochemistry Staining

Figure 26:
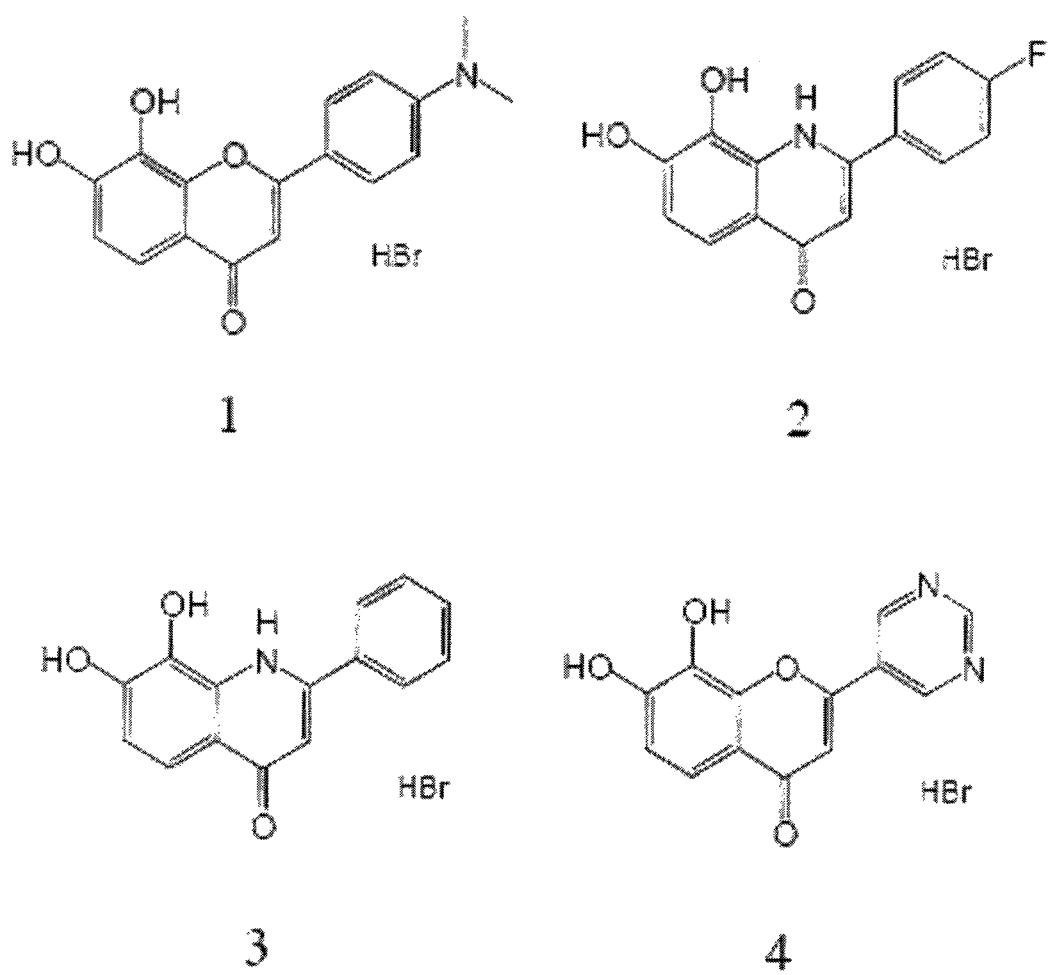
FIG. 26 shows the chemical structures of several 7,8-dihydroxyflavone derivatives.

Brain tissues were fixed in 4% paraformaldehyde overnight followed by paraffin embedding. Sections of 5 µm were cut. For immunohistochemical staining, brain sections were deparaffinized in xylene and rehydrated in graded alcohols. Endogenous peroxidase activity was blocked by 3% hydrogen peroxide for 5 minutes and all slides were boiled in 10 mM sodium citrate buffer (pH 6.0) for 10 minutes. Phosphorylated Trk A, Trk A, phosphorylated Trk B, and Trk B were detected using specific antibodies and a Zymed HistostainPlus AEC kit (Invitrogen; Carlsbad, Calif.). Slides were then counterstained with hematoxylin.
Competition Assay with 4'-dimethylamino-7,8-dihydroxyflavone Purified TrkB ECD proteins were incubated with 4'-DMA-7,8-DHF (see structure 1 of FIG. 26), 7,8-dihydroxy-2(pyrimidin-5-yl)-4H-chromen-4-one (see structure 4 of FIG. 26), and 2-(4-fluoro-phenyl)-7,8-dihydroxyquinolin-4(1H)-one (see structure 2 of FIG. 26) at 4° C. for 10 min in 1 ml of binding buffer (50 mM Na—K phosphate, pH 7.1, 200 mM NaCl and 2 nM $^3$H-7,8-DHF (68000 cpm)). After the incubation, the reaction mixture was loaded on filter paper. The mixture was washed with 3×5 ml washing buffer (100 mM Tris, pH 7.1). The dried filter paper was put into a small vial and subjected to liquid scintillation counter analysis. The values of the competition constants were calculated.
Kainic Acid/TrkB Agonists Drug Administration Male C57BL/6 mice age 60 days were orally injected with a single dose of 4'-DMA-7,8-DHF or 7,8-DHF (1 mg/kg each). KA (20 mg/kg) was i.p. injected. Animals were continually monitored for 2 hours for the onset of seizure activity. At 0, 4 and 8 hours following TrkB agonist treatment, the animals were sacrificed and the brain lysates were analyzed by immunoblotting with p-TrkB-Y817, active caspase-3 and total TrkB antibodies.
TrkB Agonists Suppress KA-induced Neuronal Cell Death in TrkB F616A Mice TrkB F616A knockin mice (2-3 months old) were fed 1NMPP1 (25 µM) in drinking water one day before pharmacological reagent treatment. The next day, the mice were orally injected with 7,8-DHF or 4'-DMA-7,8-DHF (5 mg/kg) 4 hours before kainic acid (20 mg/kg). The control mice were injected with saline, 1NMPP1, kainic acid alone or administrated 7,8-DHF or 4'-DMA-7,8-DHF 4 hours before kainic acid. In 4 days, the mice were sacrificed and brains were homogenized and ultra-centrifuged. The supernatant (40 µg) was employed for SDS-PAGE and immunoblotting analysis with indicated antibodies, respectively.
Force Swim Test Adult male mice (2-3 months old) were randomly submitted to a forced swim test without a pre-swim. Saline, 4'-DMA-7,8-DHF and 7,8-DHF (5 mg/kg) were orally injected for 21 days. The mice were allowed to adapt to the test room for 2 days. The mice were placed in a clear glass cylinder with a diameter of 16 cm, half-filled with clear water at 24° C. (water depth of 14 cm did not allow the mice to reach the bottom of the cylinder; water was changed after each mouse) for a total of 6 min, and immobility was recorded during the last 4 min by an investigator blind to the genotype and treatment.
Neurogenesis Analysis in TrkB Agonists Treated Hippocampus Adult male mice (2-3 months old) were orally injected with saline, 4'-DMA-7,8-DHF and 7,8-DHF (5 mg/kg) for 21 days. Then BrdU (50 mg/kg) was i.p. injected. In 2 hours, the mice were perfused with 4% paraformaldehyde. Immunohistochemical staining was performed on formalin-fixed paraffin-embedded sections. Sections from brain were cut, deparaffinized in xylene and rehydrated in graded alcohols. The slides were boiled in 10 mM citric acid (pH 6.0) for 10 minutes followed by an incubation in 2 N HCl for 10 minutes in room temperature. The slides were then permeabilized and blocked with 1% BSA in 0.2% PBST. The incorporated BrdU were stained using anti-BrdU-FITC (Abcam, Inc; Cambridge, Mass.) at 4° C. for 16 hours. After three washes in PBS, the cells were stained with DAPI for another 10 minutes at room temperature. The slides were mounted with AquaMount (Lerner Laboratories; Pittsburgh, Pa.) containing 0.01% 1,4-diazobicyclo(2,2,2)octane and examined under a fluorescence microscope.
Statistical Analysis All results were expressed as mean±SD. Mean ischemic Laser-Doppler Flowmetry (LDF) and lesion volume were analyzed using the Student's t-test. The criterion for statistical significance was set at p<0.05.
Other Instruments NMR spectrum (Bruker AV300K, 300 MHz (Bruker Optics Inc.; Billerica, Mass.)), MS spectrum (Shimadzu LCMS (Shimadzu Scientific Instruments; Columbia, Md.)), HPLC (PE, dual pumper, SPD detector, ODS-C18 reverse phase, 254 nm, $CH_3CN$—$H_2O$-0.1% TFA (PerkinElmer Life And Analytical Sciences, Inc.; Waltham, Mass.)).

Example 1

Figure 1B:
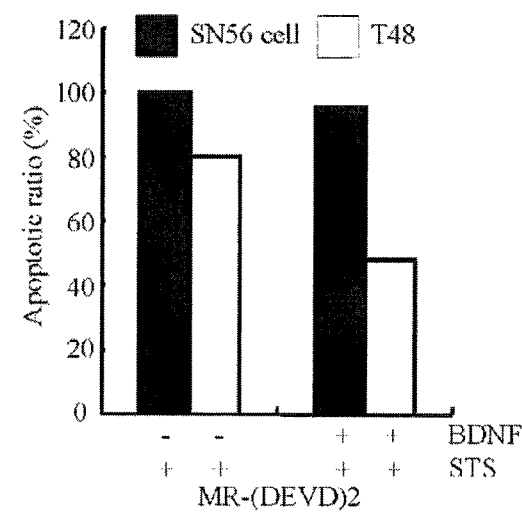
FIG. 1B shows a bar graph illustrating the results of quantitative analysis of apoptosis in stable T48 cell line.

Cell-based Screen to Identify Compounds that Protect Trkb Expressing Cells from Apoptosis Create and test reporter cell lines. In order to identify small molecules that mimic BDNF and activate TrkB, TrkB stably transfected murine cell lines were created. The T48 and T62 cell lines were created by transfecting basal forebrain SN56 cells, which express negligible TrkB, with a TrkB expression construct. To test expression of TrkB, the cells were treated with BDNF, which resulted in strong phosphorylation of Trk-490 and Akt activation in comparison to the TrkA NTR stably expressing T17 cell line (FIG. 1A), indicating expression of TrkB. To test resistance to apoptosis, SN56 cells and the T48 cell line were either untreated or treated with BDNF, and then subjected to an apoptotic assay. Briefly, the cells were treated with 0.75 µM Staurosporine for 9 hours, and 1 hour before the termination of the experiment, the cells were treated with 10 µM MR (DEVD)$_2$. The cells were then fixed with 4% paraformaldehyde for 15 minutes, washed with phosphate buffered saline (PBS), and incubated with Hoechst 33342 for 10 minutes. Cover slides were washed with PBS, mounted, and the cells were examined using a fluorescent microscope to see which cells turned red upon caspase cleavage. Treatment with BDNF decreased apoptosis in the T48 cell line as compared to the parental SN56 cell line (FIG. 1B).

Figure 2:
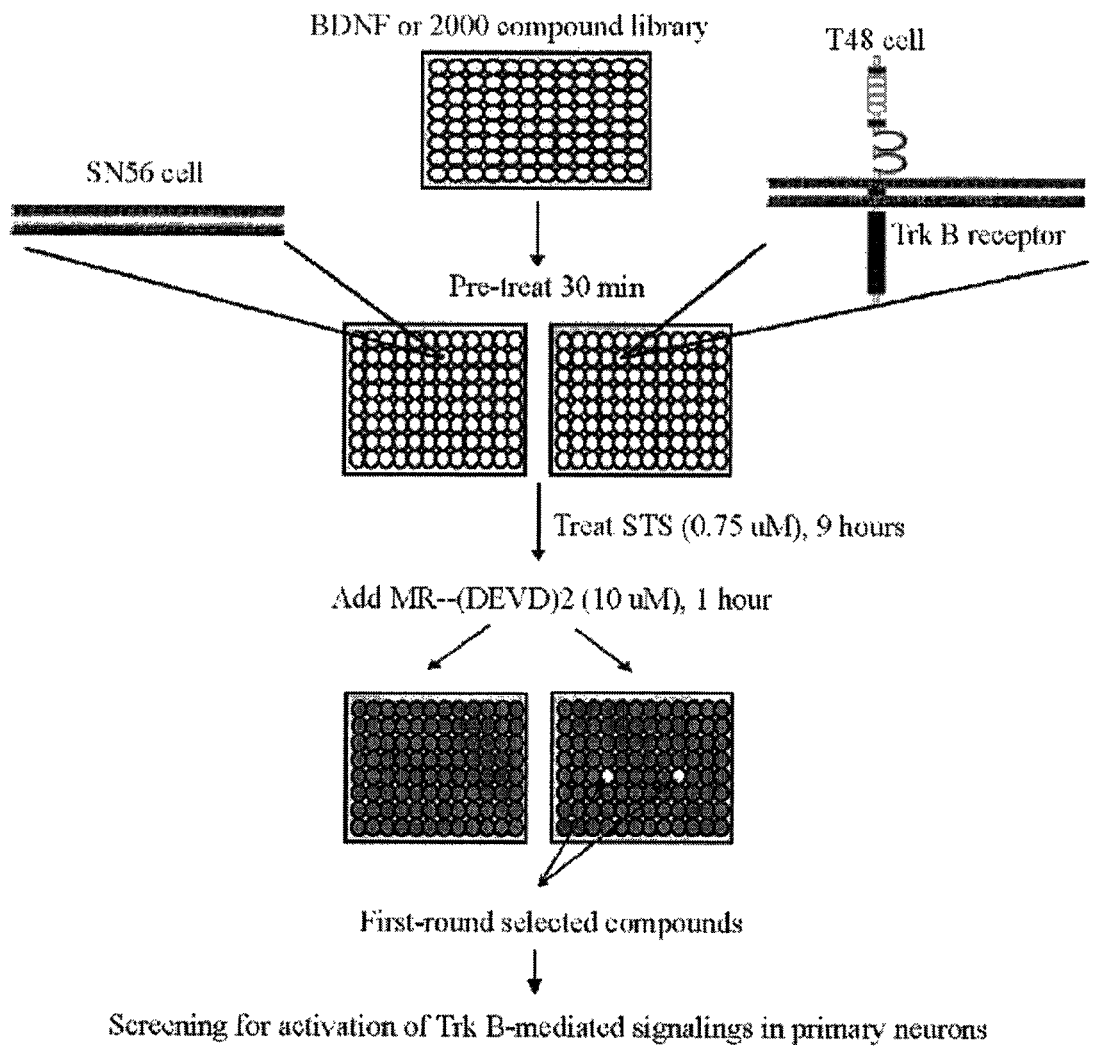
FIG. 2 shows a design for a chemical screen to identify TrkB agonists.

Cell-based screen. To screen a large number of chemicals, a cell-based apoptic assay was developed using a cell permeable fluorescent dye, MR (DEVD)2, which turns red upon caspase cleavage in apoptotic cells. SN56 and T48 cells were plated at 10,000 cells per well in multiple 96-well plates and exposed to 2000 biologically active compounds from the Spectrum Collection Library for 30 minutes at a concentration of 10 µM in DMSO. Following exposure to the compounds, the cells were subjected to the developed fluorescent apoptotic assay described above (method schematically shown in FIG. 2).

Candidates selectively protecting the T48 cell line, but not the SN56 cell line, were then subjected to a neurite outgrowth assay of SH-SY5Y cells for a secondary screen. The positive compounds were further validated for TrkB activation, PI-3 kinase/Akt and MAP kinases signaling cascade activation in primary hippocampal neurons. Sixty-six compounds selectively protected the T48 cell line but not the SN56 cell line.

Example 2

Identification of Flavone Derivatives as Survival Enhancers

Figure 3:
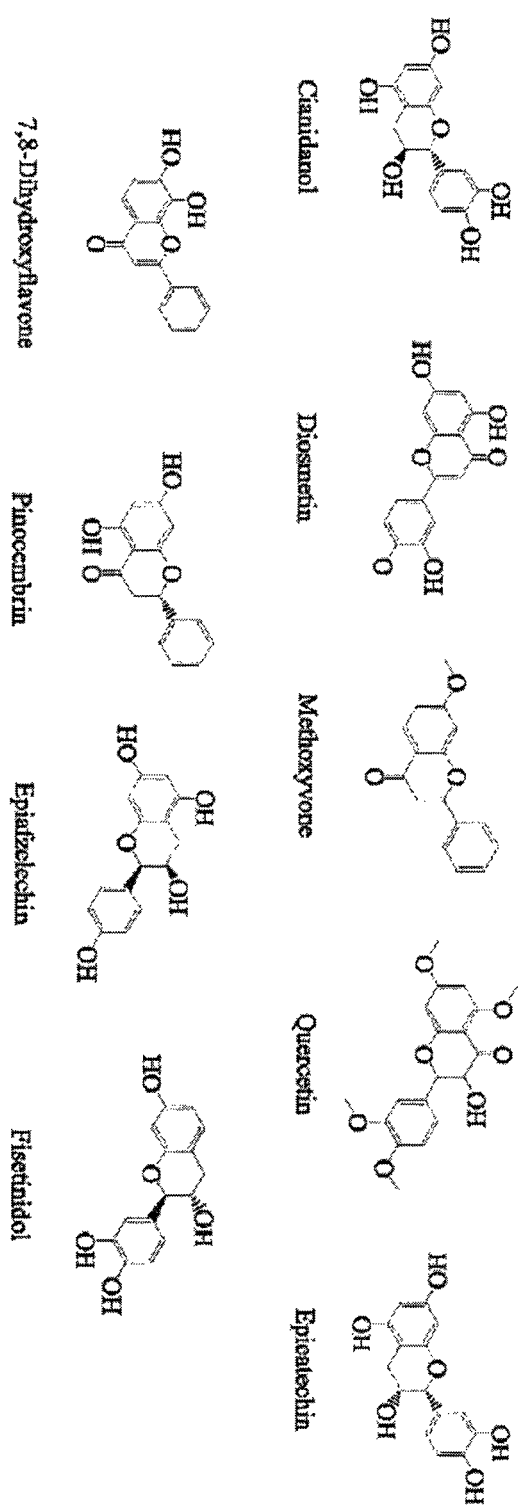
FIG. 3 shows the chemical structures of flavone derivatives.
Figure 4:
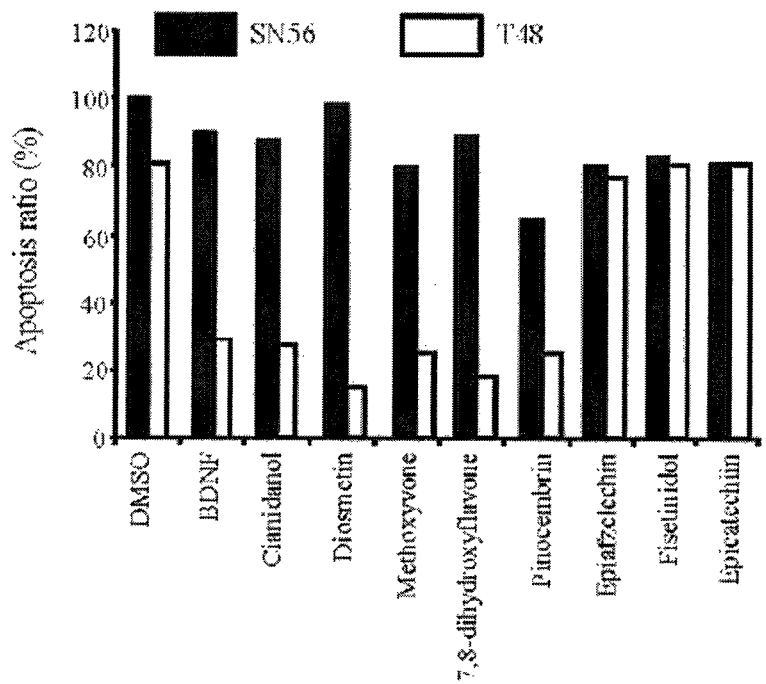
FIG. 4 shows a bar graph illustrating flavone derivatives that prevent apoptosis in T48 cells but not S56 cells.
Figure 5:
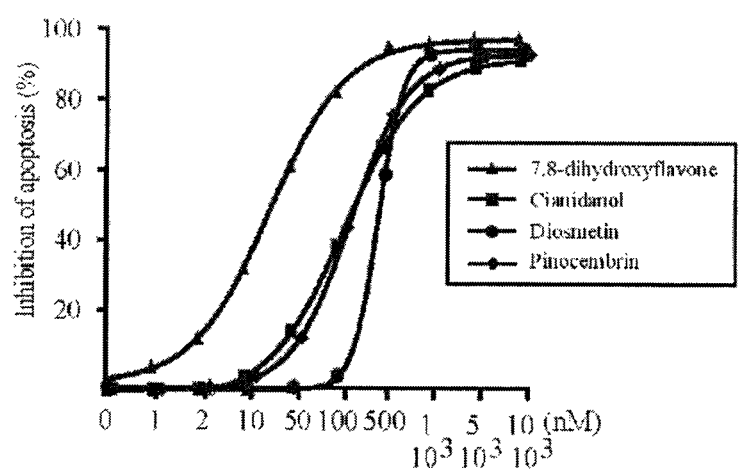
FIG. 5 shows a titration curve indicating the effective concentration for 50% apoptosis (EC50) in T48 cells.

In the initial screen, 5 of the 66 positive compounds were flavone derivatives or similar compounds. The library also contained numerous flavone derivatives that were inactive. The chemical structures of 9 representative flavone compounds are shown in FIG. 3. To compare the apoptosis inhibitory activity, the flavone derivatives were preincubated with SN56 and T48 cells, and subsequently were subjected to the fluorescent apoptotic assay as described above. In the T48 cell line, 7,8-dihydroxyflavone, Cianidanol, Diosmetin, Menadione, and Pinocembrin strongly suppressed apoptosis; however, Epiafzelechin, Fisetinidol, and epicatechin failed to suppress apoptosis (FIG. 4). Additionally, the effective concentration at which 50% (EC50) of the cells are protected from apoptosis was determined for 7,8-dihydroxyflavone, Cianidanol, Pinocembrin and Diosmetin. The EC50s of these compounds were 35, 100, 100, and 500 nM, respectively (FIG. 5).

Figure 6:
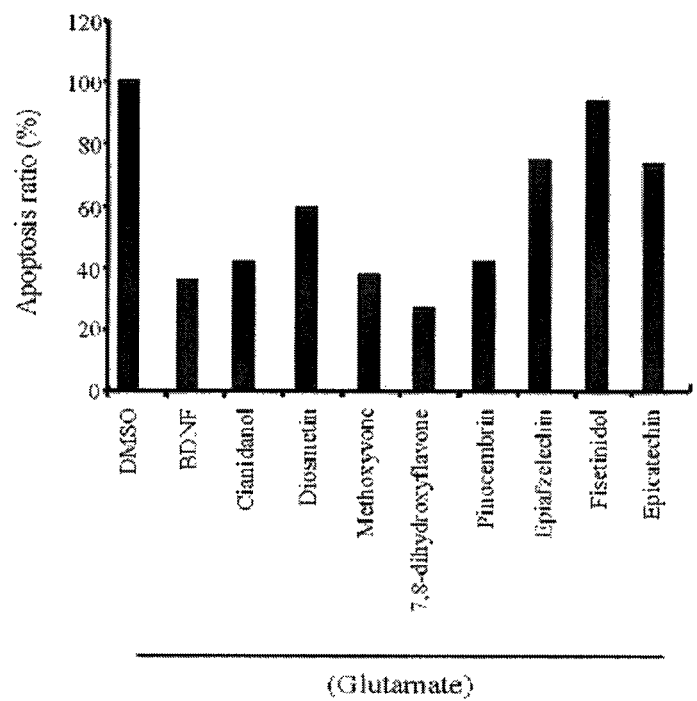
FIG. 6 shows a bar graph indicating protection by flavone derivatives of hippocampal neurons from glutamate-triggered apoptosis.

To examine whether these compounds could promote neuronal survival, hippocampal neurons were prepared and the cultures were pretreated with various flavone derivatives for 30 minutes, followed by treatment with 50 µM glutamate for 16 hours. A quantitative apoptosis assay demonstrated that 7,8-dihydroxyflavone displayed a more protective effect on the neurons than did the positive control BDNF (FIG. 6). Cianidanol, Menadione, and Pinocembrin exhibited comparable anti-apoptosis activity as BDNF; however, Diosmetin, Epiafzelechin, and Epiacatechin only slightly protected neurons from glutatmate-induced cell death and Fisetinidol showed no effect (FIG. 6).

Figure 7:
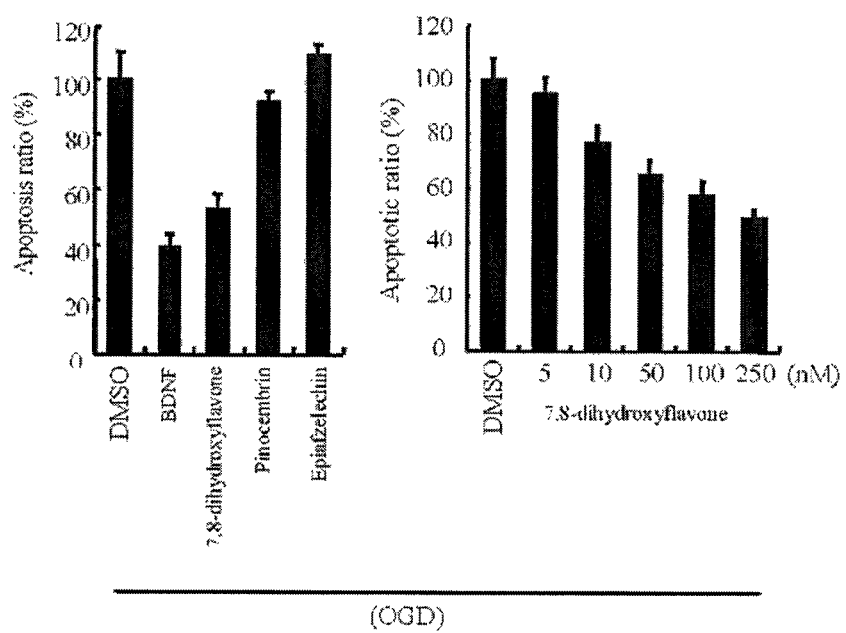
FIG. 7 shows a bar graph illustrating the ability of 7,8-dihydroxyflavone to protect against oxygen-glucose deprivation.

To explore whether 7,8-dihydroxyflavone exerts any protective effect on hippocampal neurons in Oxygen-Glucose Deprivation (OGD), primary preparations of neurons were treated with BDNF or various flavone derivatives for 30 minutes prior to OGD. In 3 hours, apoptotic analysis demonstrated that 7,8-dihydroxyflavone exhibited the most potent protective effects among the compounds (FIG. 7, left panel), and a titration assay revealed that 7,8-dihydroxyflavone protects neurons in a dose-dependent manner (FIG. 7, right panel).

Example 3

7,8-dihydroxyflavone Triggers TrkB Activation in Hippocampal Neurons in vitro

Figure 8:
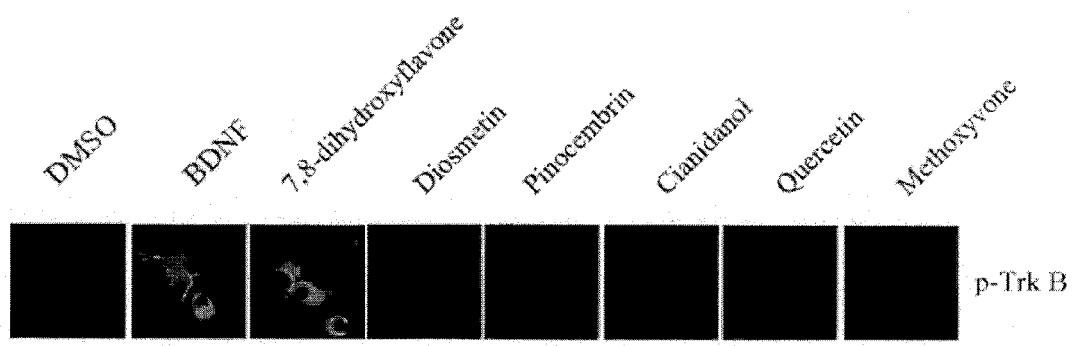
FIG. 8 shows immunofluorescent staining images showing that 7,8-dihydroxyflavone induces TrkB tyrosine phosphorylation in primary hippocampal neurons.

BDNF binding to TrkB induces its autophosphorylation and, subsequently, activation of downstream kinase pathways including MAPK and PI3/Akt. To explore whether 7,8-dihydroxyflavone triggers TrkB activation, immunofluorescent staining on hippocampal neurons with anti-phospho TrkB antibody was conducted. As shown in FIG. 8, 7,8-dihydroxyflavone, but not any of the other flavone derivatives tested, specifically provoked TrkB tyrosine phosphorylation similar to BDNF (the light areas indicating phosphorylation).

Figure 9:
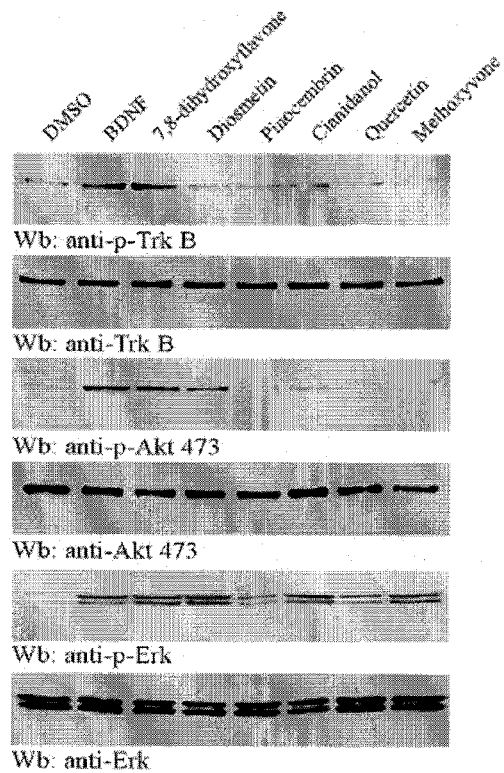
FIG. 9 shows Western blots demonstrating that 7,8-dihydroxyflavone induces TrkB phosphorylation in primary hippocampal neurons.

To further examine whether 7,8-dihydroxyflavone can stimulate TrkB-mediated downstream signaling cascades, Western analysis was performed. As shown in FIG. 9, 7,8-dihydroxyflavone again demonstrated activation of TrkB, in contrast to the other flavone derivatives. Additionally, as shown in FIG. 9, both Akt and Erk were activated by 7,8-dihydroxyflavone and Diosmetin, and Erk was activated by Pinocembrin, Cianidanol, Quercetin, and Methoxyvone.

Figure 10:
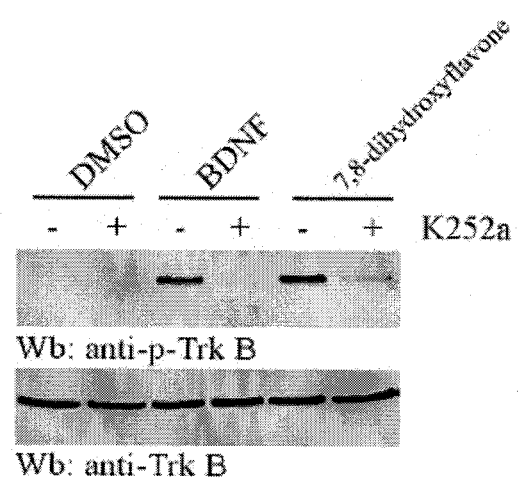
FIG. 10 shows Western blots demonstrating that K252a blocks 7,8-dihydroxyflavone's agonistic effect on TrkB.

To further test that the stimulatory effect of 7,8-dihydroxyflavone is mediated through TrkB, cells were either untreated or treated with K252a, a selective inhibitor of the tyrosine kinase activity of the Trk family of neutrophin receptors. As shown in FIG. 10, cells treated with K252a showed that K252a blocked TrkB tyrosine phosphorylation in cells exposed to 7,8-dihydroxyflavone.

Figure 11:
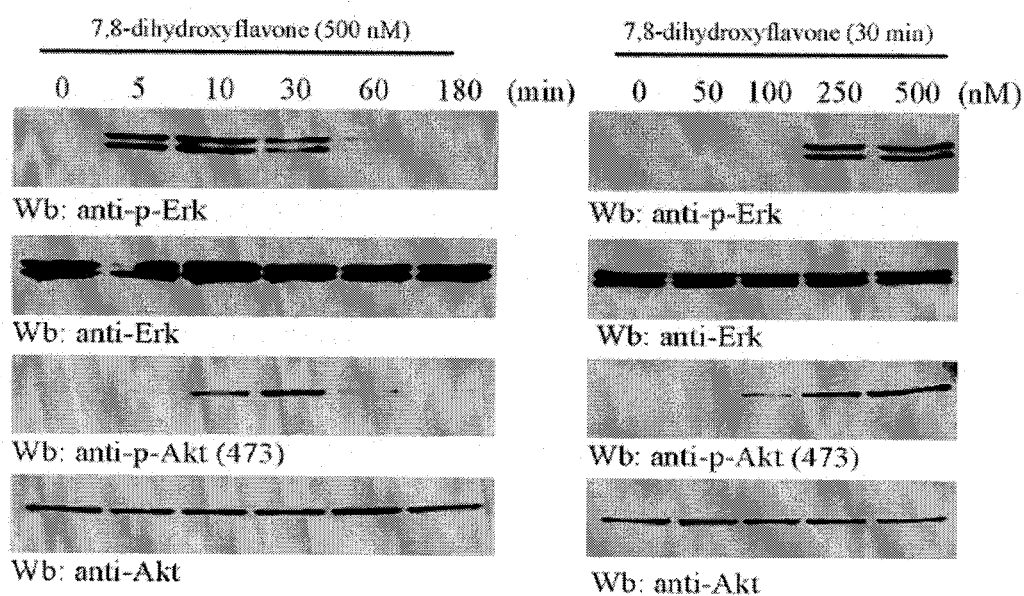
FIG. 11 shows Western blots illustrating the stimulatory effect of 500 nM 7,8-dihydroxyflavone treatment on Akt and ERK phosphorylation in hippocampal neurons for increasing amounts of time (left panel), as well as the phosphorylation of Akt and ERK in cells treated with increasing concentrations of 7,8-dihydroxyflavone (right panel).

To probe the time course of 7,8-dihydroxyflavone triggered TrkB activation, hippocampal neurons were treated with 7,8-dihydroxyflavone at 500 nM and phosphorylation of Erk and Akt was determined over time by Western analysis. As shown in FIG. 11 (left panels), Erk phosphorylation was observed at 5 minutes, increased at 10 minutes, sustained to 30 minutes, decreased by 60 minutes, and faded by 180 minutes, whereas Akt phosphorylation was seen at 10 minutes, peaked at 30 minutes, decreased at 60 minutes, and faded by 180 minutes. Stimulation of Erk and Akt by 7,8-dihydroxyflavone also occurred in a dose dependent manner. As shown in FIG. 11 (right panels), Erk phosphorylation was observed at 250 nM and increased at 500 nM, while Akt activation was observed at 100 nm and increased at 250 nM and 500 nM 7,8-dihydroxyflavone treatment for 30 minutes.

Example 4

7,8-dihydroxyflavone Triggers TrkB Activation in Hippocampal Neurons in vivo

Figure 12:
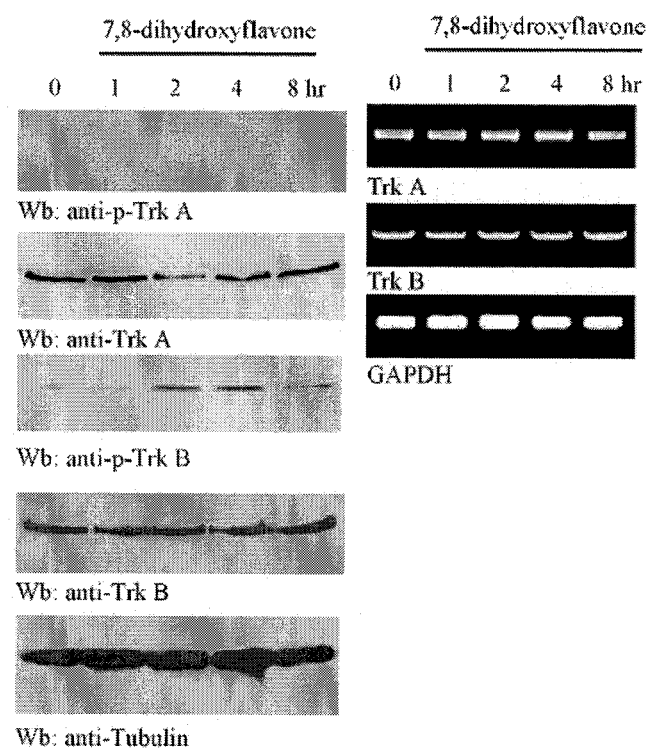
FIG. 12 shows Western blots illustrating that 7,8-dihydroxyflavone induces TrkB phosphorylation in mice brains after intraperitoneal injection (left panel), and an RT-PCR analysis demonstrating the levels of TrkA and TrkB receptor mRNA remain stable (right panel).
Figure 13:
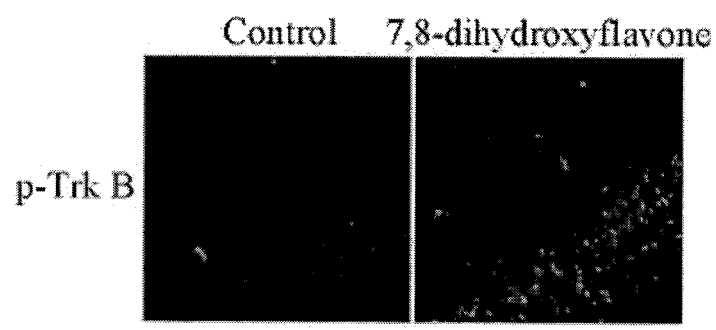
FIG. 13 shows immunofluorescent stains illustrating that 7,8-dihydroxyflavone induces TrkB phosphorylation in mouse hippocampus.

To assess whether 7,8-dihydroxyflavone can provoke TrkB activation in the brain, mice were intraperitoneally injected with a dose of 5 mg/kg and analyzed at various time points. As shown in FIG. 12 (left panel), Western analysis revealed that TrkB, but not TrkA, was selectively phosphorylated in the brain 2 hours after injection. Further, as shown in FIG. 12 (right panel), the protein and mRNA levels of the neurotrophic receptors were not altered after treatment with 7,8-dihydroxyflavone. As shown in FIG. 13, immunofluorescent staining of the brain displayed substantial TrkB phosphorylation in the hippocampus (light areas indicate phosphorylation).

Example 5

7,8-dihydroxyflavone Binds the Extracellular Domain of the TrkB Receptor

Figure 14:
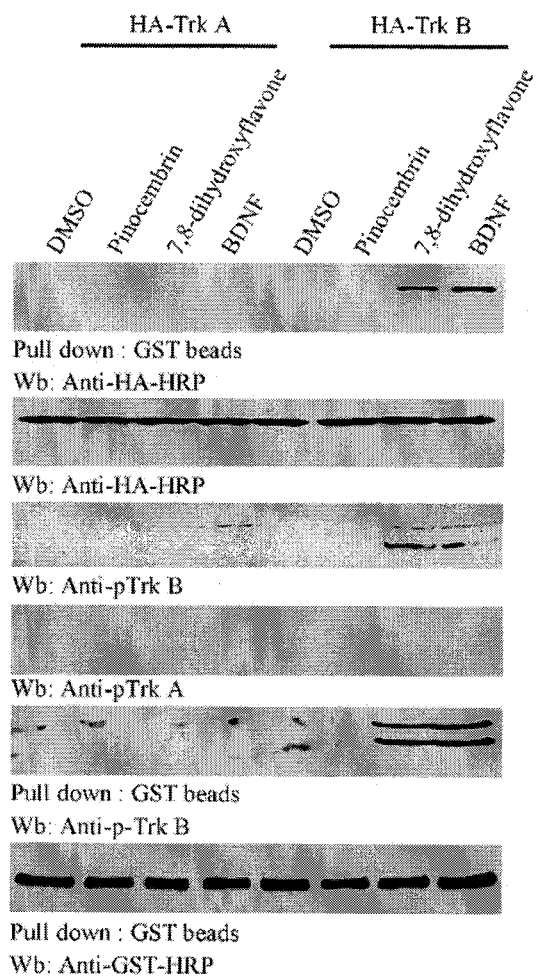
FIG. 14 shows Western blots demonstrating that 7,8-dihydroxyflavone provokes TrkB dimerization.

BDNF is known to bind the TrkB receptor and provoke its dimerization (Barbacid, J. Neurobiol., 25:1386-1403, 1994; Klein et al, Cell, 66:395-403, 1991). To explore whether 7,8-dihydroxyflavone triggers TrkB receptor dimerization, HEK293 cells were cotransfected with GST-TrkB and HA-TrkB or HA-TrkA. The cells were then treated with BDNF or small flavone compounds (0.5 µM) for 30 minutes. The cells were harvested, washed once in PBS, and lysed in 1 ml lysis buffer (50 mM Tris, ph 7.4, 150 mM NaCl, 1 mM EDTA, 0.5% Triton X-100, 1.5 mM $Na_3VO_4$, 50 mM NaF, 10 mM sodium pyrophosphate, 10 mM sodium β-glycerophosphate, 1 mM phenylmethylsulfonyl fluoride (PMSF), 5 mg/ml aprotinin, 1 mg/ml leupeptin, 1 mg/ml pepstatin A) and centrifuged for 10 minutes at 14,000×g at 4° C. The supernatant was transferred to a fresh tube and transfected TrkB receptor was separated from the supernatant with glutathione beads, and the coprecipitated proteins were resolved on SDS-PAGE. The samples were transferred to nitrocellular membrane, and western analysis demonstrated that 7,8-dihydroxyflavone provoked TrkB dimerization to a similar manner as BDNF, whereas the inactive flavone, Pinocembrin, and DMSO failed (FIG. 14). By contrast, the cotransfected TrkB receptor failed to dimerize with TrkA receptor regardless of BDNF or 7,8-dihydroxyflavone treatment.

Figure 15:
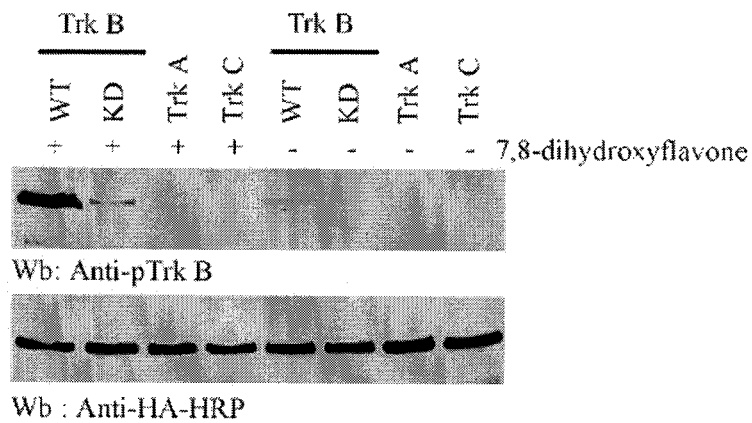
FIG. 15 shows Western blots indicating that 7,8-dihydroxyflavone induces TrkB autophosphorylation.

To determine if 7,8-dihydroxyflavone promoted tyrosine phosphorylation of the other Trk receptors, HEK293 cells were transfected with various Trk receptors, followed by treatment with 7,8-dihydroxyflavone. As shown in FIG. 15, treatment with 7,8-dihydroxyflavone elicited tyrosine phosphorylation in the TrkB receptor but not in the TrkA or TrkC receptor. Negligible tyrosine phosphorylation was observed in the kinase-dead (KD)-TrkB receptor.

Figure 16:
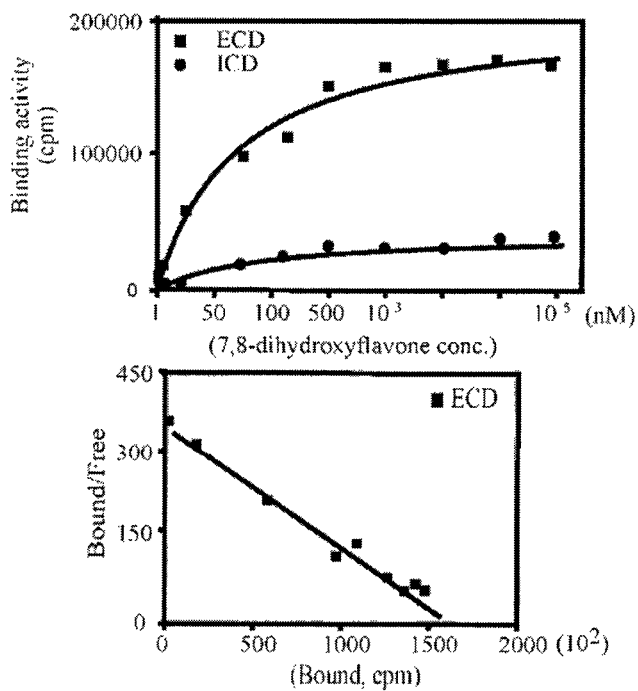
FIG. 16 shows the results of an in vitro binding assay with purified TrkB extracellular domain (ECD) or intracellular domain (ICD) (10 µg) and [$^3$H]7,8-dihydroxyflavone illustrating that [$^3$H]7,8-dihydroxyflavone binds the ECD but not ICD of TrkB receptor (upper panel), and Scatchard plot analysis of these data indicates that 7,8-dihydroxyflavone binds TrkB with a binding constant of 320 nM (lower panel).

To determine whether 7,8-dihydroxyflavone physically and directly binds the TrkB receptor, in vitro binding assays were conducted with purified TrkB extracellular domain (ECD) and intracellular domain (ICD) recombinant proteins. Purified TrkB ECD and ICD (10 μg of each) were incubated with different concentrations of $^3$H-7,8-dihydroxyflavone in 1 ml of binding buffer (0.05M Na/K phosphate buffer, pH 7.1, 200 mM NaCl) at 4° C. for 10 minutes. After the incubation, the reaction mixture was loaded on filter paper. The mixture was washed three times with Tris buffer (100 mM Tris, pH 7.1), and the dried filter paper was put into a small vial and subjected to liquid scintillation counter analysis. Gradual increments of [$^3$H]-7,8-dihydroxyflavone progressively bound TrkB ECD but not ICD. The value of the dissociate constant and the number of sites were obtained from Scatchard plots using the equation $r/[L]_{free}=n/K_d-r/K_d$, where r is the ratio of the concentration of bound ligand to the total protein concentration and n is the number of binding sites. Quantitative analysis using the Scatchard plot revealed that the ratio of ligand to the receptor is 1:1 with a binding constant $K_d$ of 320 nM (see FIG. 16). Neither the ECD nor ICD of TrkA receptor was capable of binding 7,8-dihydroxyflavone.

Figure 17:
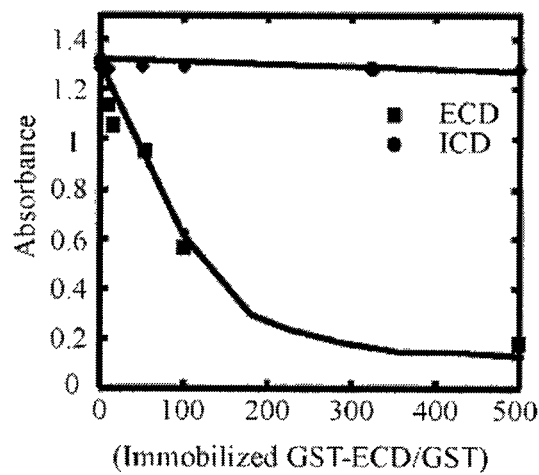
FIG. 17 shows a graph illustrating the results of an in vitro binding assay with immobilized GST-TrkB ECD or ICD and 7,8-dihydroxyflavone.

To further explore the association of 7,8-dihydroxyflavone and the TrkB receptor, an in vitro binding assay was performed. Increasing volumes of GST-TrkB ECD and GST-TrkB ICD were bound to glutathione beads to a total of 250 uL, and 500 nM 7,8-dihydroxyflavone in 250 μl (20% DMSO/80% PBS) was incubated with the beads in the column at 4° C. for 30 minutes. After the incubation, the elute fractions were collected and the concentration of eluted 7,8-dihydroxyflavone was analyzed by UV-spectrometry at a wavelength of 410 nm. As shown in FIG. 17, the concentration of 7,8-dihydroxyflavone decreased as GST-TrkB ECD volumes increased; however, as GST-TrkB ICD volumes increased, the concentration of eluted 7,8-dihydroxyflavone remained constant.

Figure 18:
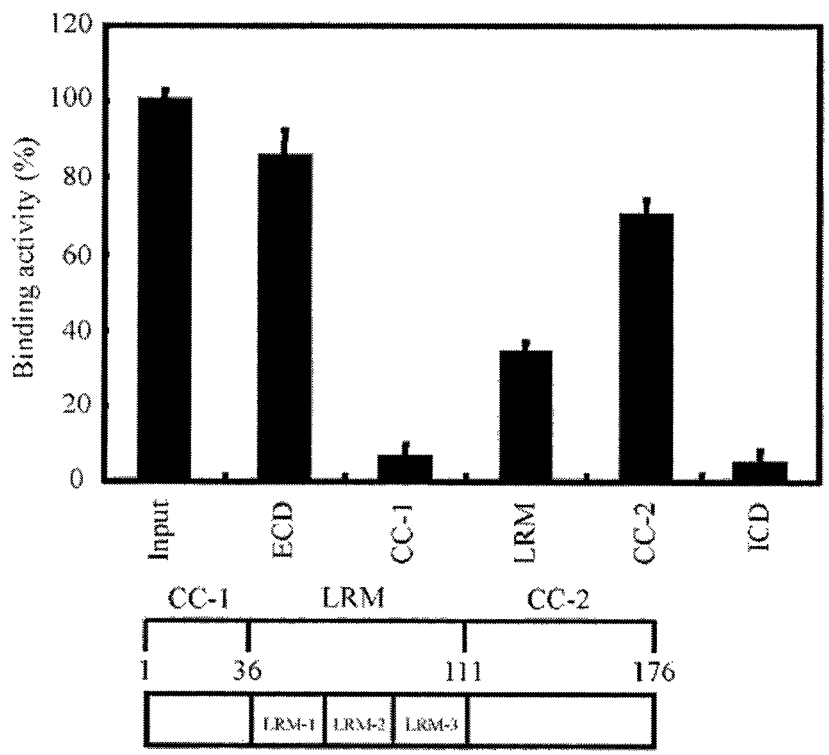
FIG. 18 shows the results of a mapping assay with various ECD truncates and [$^3$H]7,8-dihydroxyflavone.

BDNF is known to bind to the region of the TrkB ECD that contains the third leucine-rich motif (LRM), the second cysteine cluster (CC) domain, and the Immunoglobulin 2 (Ig2) domain (Haniu et al., J. Biol. Chem., 272:25296-303, 1997). To map where 7,8-dihydroxyflavone binds on the TrkB ECD, truncation mutants of the ECD were made and in vitro binding assays were conducted. As shown in FIG. 18, 7,8-dihydroxyflavone strongly associated with the ECD and the CC-2 domain, associated less strongly with the LRM-domain, and did not bind the CC-1 domain or the ICD.

Example 6

Figure 19:
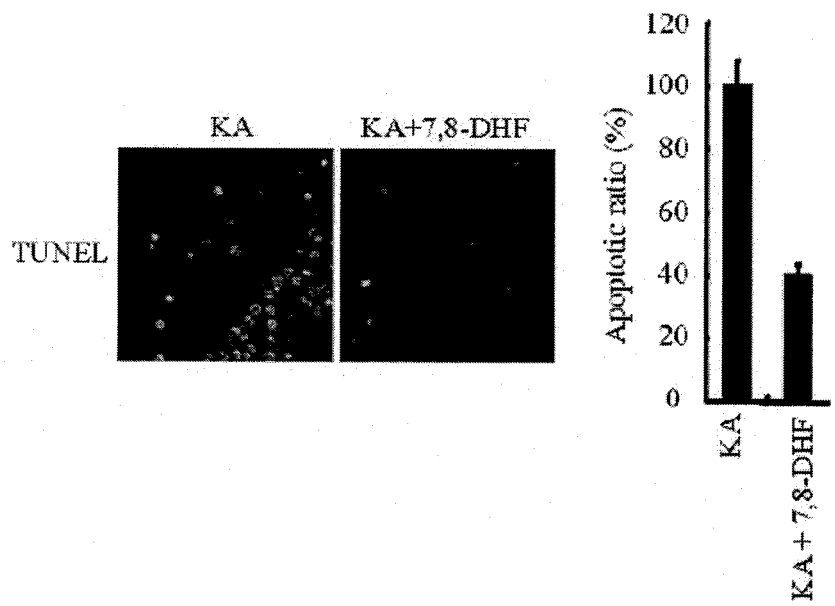
FIG. 19 shows TUNEL assay results of brain slides indicating 7,8-dihydroxyflavone decreases KA-induced apoptosis in mouse brain (left panel), and a quantitative analysis of apoptosis in the hippocampus (right panel).

7,8-dihydroxyflavone Prevents Kainic Acid-triggered Neuronal Apoptosis and Decreases Infarct Volume of Stroked Rat Brain Kainic acid (KA) is a potent agonist for the AMPA receptor. Peripheral injections of KA result in recurrent seizures and the subsequent degeneration of select populations of neurons in the hippocampus (Schauwecker and Steward, Proc. Natl. Acad. Sci. USA, 94:4103-8, 1997). KA induces neuronal cell death in a caspase-dependent and independent manners (Faherty et al., Brain Res. Mol. Brain. Res., 70:159-63, 1999; Glassford et al., Neurol. Res., 24:796-800, 2002; Liu et al., Mol. Cell, 29:665-78, 2008). To explore whether 7,8-dihydroxyflavone can block the neurotoxicity initiated by KA, C57BL/6 mice aged 60 days were intraperitoneally injected with either a single dose of 20% DMSO in saline, 20 mg/kg KA (Sigma), or 5 mg/kg of 7,8-dihydroxyflavone followed by 20 mg/kg of KA. In 5 days, the mice were anesthetized, perfused with 4% paraformaldehyde in 0.1M phosphate buffered saline, and the brains were removed, post-fixed overnight, and processed for paraffin embedding. Serial sections of the brain were cut to a thickness of 5 μm and mounted on slides (Superfrostplus, Fisher; Pittsburgh, Pa.). As shown in FIG. 19 (left panel), TUNEL staining revealed that KA provoked apoptosis in the hippocampus, which was diminished by 7,8-dihydroxyflavone (light areas indicating apoptotic cells in the upper panels). Quantitative analysis of apoptosis in the hippocampus revealed that 7,8-dihydroxyflavone decreased KA-induced apoptosis in hippocampus (FIG. 19, right panel).

Figure 20:
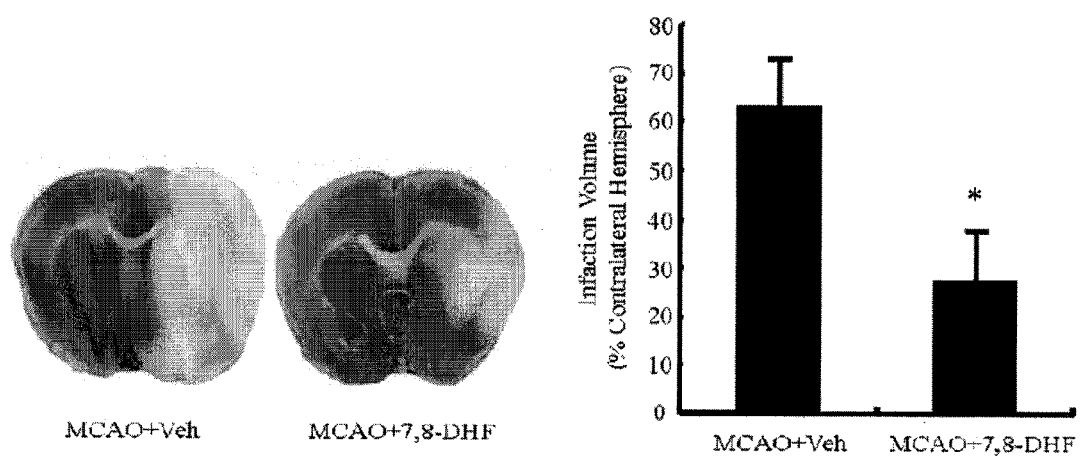
FIG. 20 shows 2,3,5-triphenyltetrazolium chloride (TTC)-stained coronal section from brains of representative animals given either vehicle (60% DMSO) or 7,8-dihydroxyflavone with infarcts shown as pale, unstained regions involving striatum and overlying cortex (left panel), and infarct volumes 24 hours after middle cerebral artery occlusion (MCAO) (right panel).

To further determine the neuroprotective potential in vivo, 7,8-dihydroxyflavone was tested in a transient middle cerebral artery occlusion (MCAO) stroke model in adult male rats. Focal cerebral ischemia was induced by occlusion of the right middle cerebral artery as previously described (Sayeed et al, Ann. Emerg. Med., 47:381-9, 2006). After 2 hours MCAO followed by reperfusion, the animals received vehicle or 7,8-dihydroxyflavone (5 mg/kg) intraperitoneally 5 minutes prior to the onset of reperfusion. All animals included in the study survived the ischemic insult and treatment with 7,8-dihydroxyflavone. A representative brain slice stained with 2,3,5-triphenyltetrazolium chloride (TTC) 24 hours after MCAO in vehicle-treated and 7,8-dihydroxyflavone-treated rats is shown in FIG. 20 (left panel). Area and volume measurements from TTC sections indicated that treatments with 7,8-dihydroxyflavone reduced infarct volumes in this transient ischemic model of stroke (FIG. 20, right panel). The data represented as mean±SD; *($p<0.05$)=significant difference compared to MCAO+Vehicle (right panel).

Example 7

7,8 dihydroxyflavone Protects Neurons from Apoptosis in TrkB Dependent Manner

Figure 21:
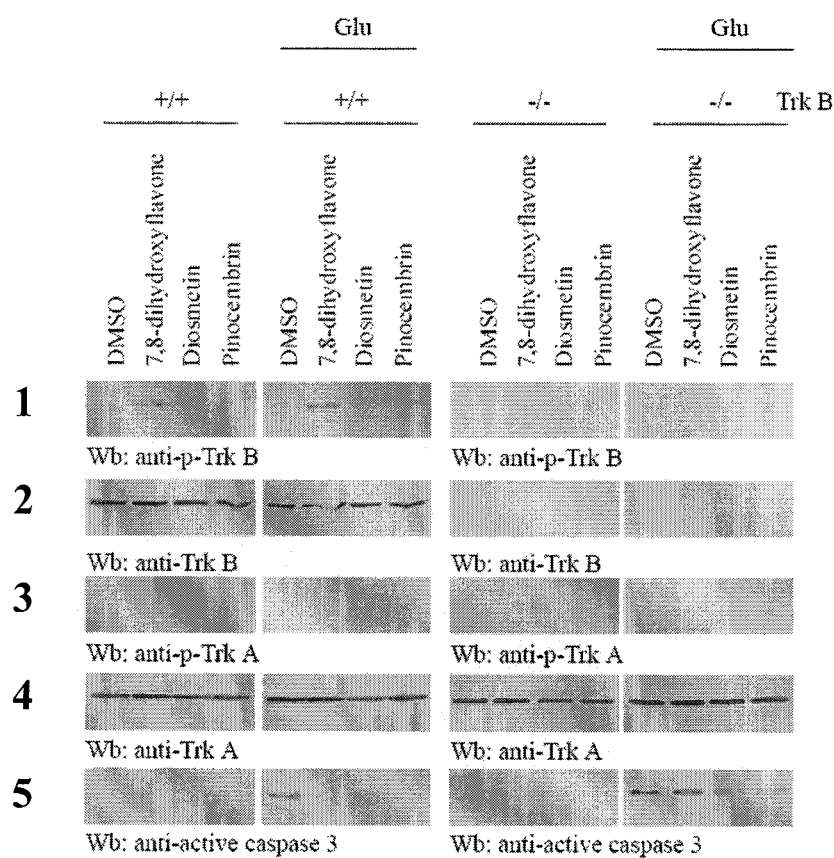
FIG. 21 shows Western blots illustrating that 7,8-dihydroxyflavone prevents glutamate-triggered neuronal apoptosis in wild-type but not TrkB null neurons.

To determine whether 7,8-dihydroxyflavone can selectively activate TrkB receptor and prevent neuronal cell death, cortical neurons were prepared from homozygous pups of TrkB+/−mice, which were mated to the same genotype. As shown in FIG. 21 (rows 1 and 3), 7,8- dihydroxyflavone specifically activates TrkB but not TrkA receptor in wild-type but not TrkB-null neurons. Glutamate nonselectively elicited weak TrkA phosphorylation in both wild-type and TrkB-null neurons (FIG. 21, row 3). Glutamate-provoked Caspase-3 activation was substantially blocked by 7,8-dihydroxyflavone in wild-type but not TrkB−/− neurons (FIG. 21, row 5). The control compounds, Diosmetin and Pinocembrin, non-selectively suppressed caspase-3 activation in both neurons (FIG. 21, row 5).

Figure 22:
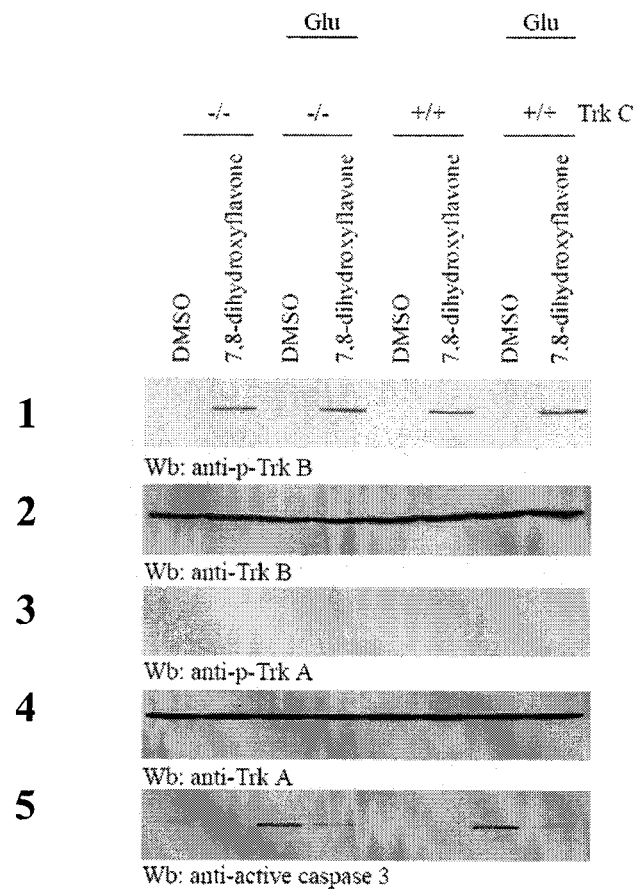
FIG. 22 shows Western blots demonstrating that 7,8-dihydroxyflavone diminishes caspase-3 activation regardless of TrkC genotype.

To further assess whether 7,8-dihydroxyflavone blocks neuronal apoptosis in a TrkB dependent manner, cortical neurons were prepared from homozygous pups of TrkC+/− mice, which were mated to the same genotype. As shown in FIG. 22 (row 1), 7,8-dihydroxyflavone provoked TrkB but not TrkA activation in both wild-type and TrkC knockout neurons. Glutamate weakly stimulated both TrkA and TrkB faint phosphorylation regardless of TrkC genotype (FIG. 22, rows 1 and 3). The spontaneous caspase-3 activation in TrkC−/− neurons was suppressed by 7,8-dihydroxyflavone (FIG. 22, row 5). Further, glutamate-triggered caspase-3 activation was significantly diminished by 7,8-dihydroxyflavone (FIG. 22, row 5).

Figure 23:
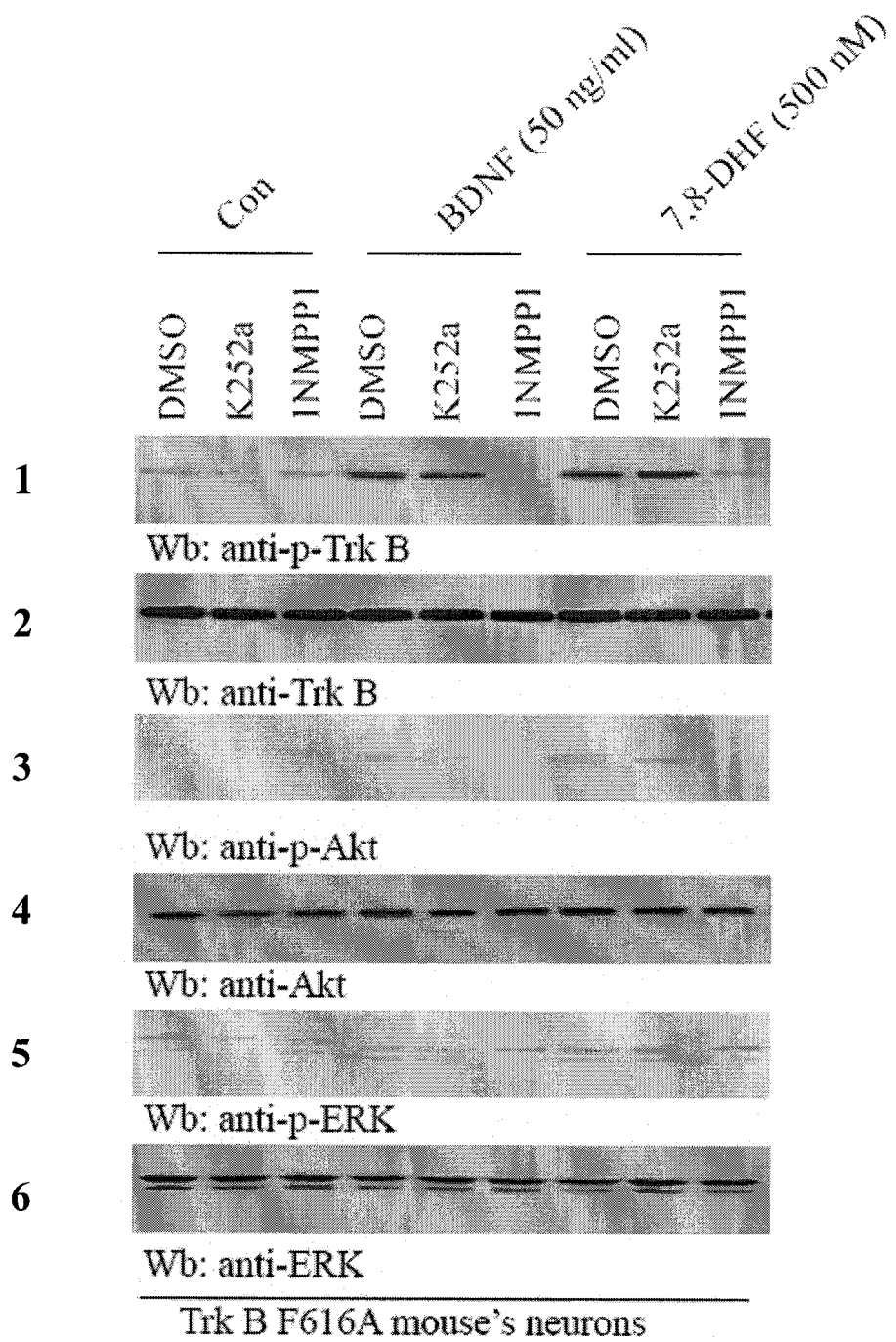
FIG. 23 shows Western blots demonstrating that 7,8-dihydroxyflavone selectively activates TrkB F616A, which can be blocked by 1NMPP1.

To explore whether the neuroprotective action of 7,8-dihydroxyflavone is dependent on TrkB activation in vivo, TrkB F616A knockin mice were used. The TrkB F616A receptor has been shown to be selectively blocked by 1NMPP1 inhibitor and lead to TrkB-null phenotypes (Chen et al., Neuron, 46:13-21, 2005). To further assess whether 7,8-dihydroxyflavone can mimic BDNF, cortical neurons were prepared from TrkB F616A knockin mice. The cortical neurons were pretreated for 30 minutes with either K252a Trk tyrosine kinase inhibitor (100 nM) or 1NMPP1 inhibitor (100 nM) followed by 0.5 μM 7,8-dihydroxyflavone for 30 minutes. As shown in FIG. 23 (row 1), BDNF-provoked TrkB phosphorylation was selectively blocked by 1NMPP1, but not K252a. 7,8-dihydroxyflavone was additionally observed to be selectively blocked by 1NMPP1, but not K252a (FIG. 23, row 1). 1NMPP1, but not K252a, blocked BDNF-triggered Akt and Erk1/2 activation, whereas 1NMPP1 partially decreased Akt activation and failed to inhibit Erk1/2 activation by 7,8-dihydroxyflavone (FIG. 23, rows 3 and 5).

Figure 24:
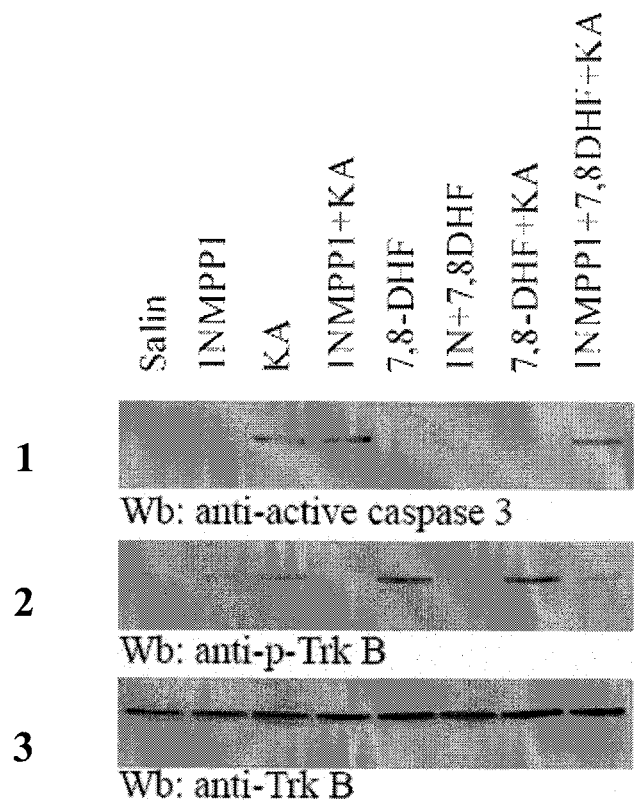
FIG. 24 shows Western blots illustrating that 7,8-dihydroxyflavone suppresses KA-induced neuronal cell death in TrkB F616A mutant mice.

To determine if 1NMPP1 would make neurons treated with 7,8-dihydroxyflavone vulnerable to KA-provoked neuronal cell death, TrkF616A knockin mice were fed with 1NMPP1 (25 mM) in drinking water one day prior to pharmacological reagent treatment. The next day, the mice were intraperitoneally injected with KA (25 mg/kg), or 7,8-dihydroxyflavone (5 mg/kg) 4 hours prior to KA injection. The control mice were injected with either KA or 7,8-dihydroxyflavone alone, or the mice were administered 7,8-dihydroxyflavone 4 hours before KA. In 4 days, the mice were sacrificed and the brains were homogenated and ultracentrifuged. The supernatant was employed for SDS-PAGE and immunoblotting analysis. As shown in FIG. 24, 1NMPP1, 7,8-dihydroxyflavone alone or 1NMPP1 and 7,8-dihydroxyflavone combined treatment had no effect on apoptosis in TrkB F616A mice. KA provoked evident caspase-3 activation, and pretreatment of 1NMPP1 elevated KA-provoked apoptosis in TrkBF616A. 7,8-dihydroxyflavone suppressed KA-provoked apoptosis, whereas 1NMPP1 pretreatment abolished 7,8-dihydroxyflavone's protective effect in F616A mice.

Example 8

7,8-dihydroxyflavone Displays an Anti-depressive Effect

Figure 25:
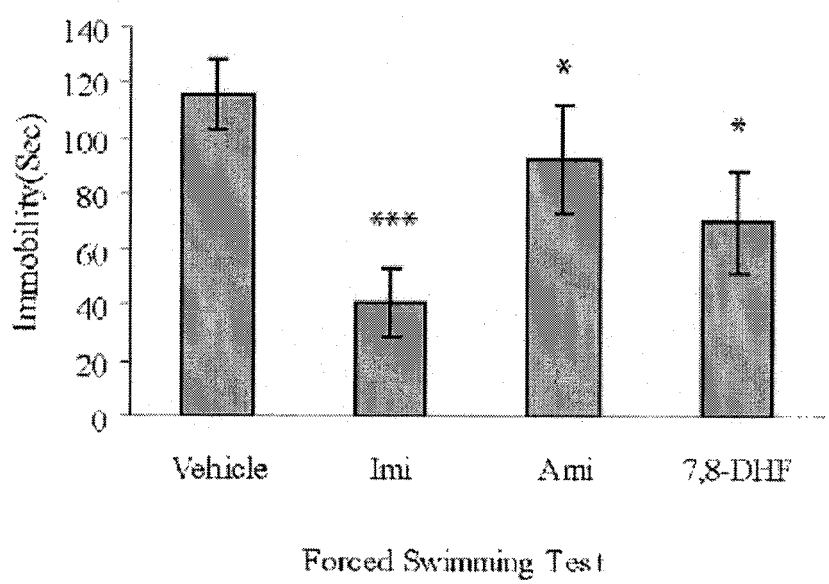
FIG. 25 is a bar graph showing the results of forced swim test behavior of mice treated with vehicle (20% DMSO/80% saline or 100% saline), imipramine, amitryptyline, or 7,8-dihydroxyflavone.

BDNF has been shown to play an essential role in mediating antidepressants' therapeutic effects (Castren, Curr. Opin. Pharmacol., 4:58-64, 2004; Duman, Biol. Psychiatry, 56:140-5, 2004; Groves, Mol. Psychiatry, 12:1079-88, 2007; Monteggia et al., Proc. Natl. Acad. Sci. USA, 101:10827-32, 2004; Saarelainen et al., J. Steroid Biochem. Mol. Biol., 78:231-9, 2003). Further, infusion of exogenous BDNF into hippocampus or brain stem has been shown to have an anti-depressant-like behavioral effect (Shirayama et al., J. Neurosci., 22:3251-61, 2002; Siuciak et al., Pharmacol. Biochem. Behav., 56:131-7, 1997). To explore whether 7,8-dihydroxyflavone has an antidepressant effect like BDNF, a forced swim test was conducted. Adult male mice (2-3 months old, n=8) were randomly submitted, without a pre-swim, to a forced swim test of 6 minutes with immobility recorded in the last 4 minutes. Mice were injected intraperitoneally for 5 days with saline, imipramine (20 mg/kg), amitryptyline (15 mg/kg), or 7,8-dihydroxyflavone (5 mg/kg). The mice were allowed to adapt to the test room for 2 days, and the mice were placed in a clear glass cylinder with a diameter of 16 cm, half-filled with clear water at 24° C. The water depth of 14 cm did not allow the mice to reach the bottom of the cylinder, and the water was changed after each mouse. As shown in FIG. 25, when the mice were treated with imipramine or amitryptyline, the swimming immobility was decreased. Additionally, 7,8-dihydroxyflavone also reduced the immobility. Data are presented as mean±SEM; *p<0.05 against vehicle, P<0.01 against vehicle and *P<0.0001 against vehicle, student t-test.

Example 9

Synthesis of 2-(4-dimethylamino)phenyl)-7,8-dihydroxyflavone.HBr $^1$H and $^{13}$C NMR spectra were recorded with a Varian 300 spectrometer (Varian, Inc.; Palo Alto, Calif.). NMR chemical shifts are reported as d values (parts per million, ppm). Infrared spectra were recorded on a Bruker Equinox 55 FTIR spectrophotometer (Bruker Optics Inc.; Billerica, Mass.). IR peaks are reported in $cm^{-1}$. Melting points were obtained with a Barnstead Electrothermal MelTemp apparatus (Thermo Fisher Scientific Inc.; Waltham, Mass.). ESI-MS spectra were recorded on an Applied Biosystems 4000 QTrap spectrometer (Applied Biosystems Inc,; Foster City, Calif.). Gallacetophenone 3',4'-dimethyl ether (1) and 4-dimethylaminobenzoyl chloride (2) were purchased from Sigma Aldrich (Sigma-Aldrich Corp.; St. Louis, Mo.). All other reagents and solvents were purchased from commercial sources and purified by standard procedures. All reactions were performed under a dry $N_2$ atmosphere in flame-dried glassware.

Using a variation of Scheme 1 above, 2-(4-dimethylamino)phenyl)-7,8-dihydroxyflavone.HBr was synthesized as follows:

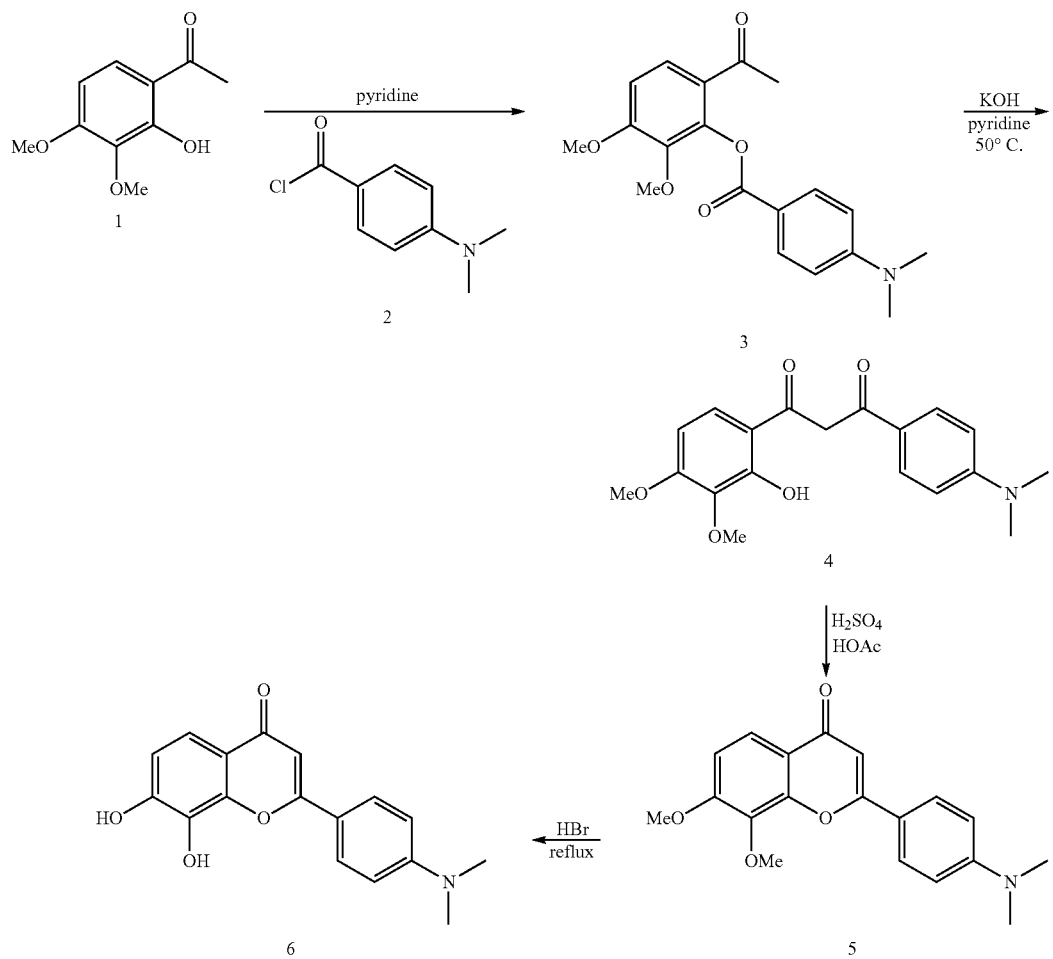

First, 6-acetyl-2,3-dimethoxyphenyl 4-(dimethylamino) benzoate (3) was synthesized as follows: To a solution of gallacetophenone 3',4'-dimethyl ether (1) (5.83 g, 29.72 mmol) in dry pyridine (25 mL) was added (4-dimethylamino)benzoyl chloride (2) (8.19 g, 44.58 mmol) in three portions over 15 minutes. The mixture was stirred at room temperature for 2 hours. The reaction was acidified with 2M HCl and extracted with ethyl acetate. The combined organics were washed with brine, dried with MgSO$_4$, and concentrated under reduced pressure. The crude product is purified by flash chromatography (10% EtOAc/hexanes) to afford 8.45 g (83%) of 3 as a white crystalline solid: mp 102-106° C.; IR (neat) 2990, 2966, 2890, 2823, 1685, 1603, 1268, 1187 cm$^{-1}$; $^1$H (CDCl$_3$) δ 8.10 (d, J=9 Hz, 2H), 7.68 (d, J=9 Hz, 1H), 6.87 (d, J=9 Hz, 1H), 6.72 (d, J=9 Hz, 2H), 3.93 (s, 3H), 3.80 (s, 3H), 3.08 (s, 6H), 2.49 (s, 3H); $^{13}$C (CDCl$_3$) 196.5, 165.0, 157.4, 154.1, 145.3, 141.7, 132.5, 125.8, 125.6, 115.6, 111.1, 109.2, 61.1, 56.4, 40.3, 30.6; ESI-MS m/z 344.11 [(M+H)$^+$].

Then 1-(4-(Dimethylamino)phenyl)-3-(2-hydroxy-3,4-dimethoxyphenyl)propane-1,3-dione (4) was synthesized as follows: A solution containing 6-acetyl-2,3-dimethoxyphenyl 4-(dimethylamino)benzoate 3 (8.45 g, 24.6 mmol), anhydrous powdered potassium hydroxide (2.08 g, 36.9 mmol), and pyridine (50 mL) was heated at 50° C. for 2 hours. The reaction was cooled to room temperature, acidified with 2M HCl, extracted with ethyl acetate, washed with brine, dried with MgSO$_4$, and evaporated under reduced pressure to yield 7.59 g (90%) of crude propanedione 4. The crude reaction mixture was carried forward without further purification. $^1$H (CDCl$_3$) δ 7.84 (d, J=9 Hz, 2H), 7.53 (d, J=9 Hz, 1H), 6.70 (d, J=9 Hz, 2H), 6.51 (d, J=9 Hz, 1H), 4.5 (s, 2H), 3.93 (s, 3H), 3.91 (s, 3H), 3.08 (s, 6H).

Next 2-(4-(Dimethylamino)phenyl)-7,8-dimethoxy-4H-chromen-4-one (5) was synthesized as follows: A solution of 1-(4-(dimethylamino)phenyl)-3-(2-hydroxy-3,4-dimethoxyphenyl)propane-1,3-dione (4) (11.5 g, 33.4 mmol) in glacial acetic acid (100 mL) and concentrated sulfuric acid (1 mL) was refluxed for 1 hour. The reaction mixture was then poured into ice and extracted with ethyl acetate. The combined organics were washed with brine, dried with MgSO$_4$ and concentrated under reduced pressure to yield a dark solid. Flash column chromatography (30% EtOAc/hexane) yielded 6.41 g (60%) as a yellow-brown solid. IR (neat) 2567, 2176, 2018, 1966, 1951, 1598, 1383, 1116 cm$^{-1}$; $^1$H (CDCl$_3$) δ 7.95 (d, J=9 Hz, 1H), 7.85 (d, J=9 Hz, 2H), 7.01 (d, J=9 Hz, 1H), 6.78 (d, J=9 Hz, 2H), 6.65 (s, 1H), 4.04 (s, 3H), 3.99 (s, 3H), 3.08 (s, 6H); $^{13}$C(CDCl$_3$) d 178.1, 156.5, 153.0, 127.9, 121.0, 111.9, 109.8, 104.0, 63.7, 57.2, 40.3; ESI-MS m/z 326.2 [(M+H)$^+$].

Then 4'-Dimethylamino-7,8-dihydroxyflavone (6) (see also structure 1 in FIG. 26) was synthesized as follows: A solution of 2-(4-(dimethylamino)phenyl)-7,8-dimethoxy-4H-chromen-4-one (5) (0.462 g, 1.42 mmol) in aqueous hydrobromic acid (48%, 10 mL) is refluxed overnight. After cooling, the reaction mixture is diluted with water, neutralized with saturated NaHCO$_3$, and extracted with 1-butanol. The organic phase is washed with water, dried with MgSO$_4$, and evaporated under reduced pressure. Recrytallization from 50% methanol/dichloromethane provided 0.221 g (52%) of 6 as deep red solid crystals: mp 242-245° C.; IR (neat) 3371, 3200, 2590, 2171, 1966, 1619, 1566, 1480, 1300 cm$^{-1}$; $^1$H NMR (DMSO-d$_6$) δ 7.97 (d, J=9 Hz, 2H), 7.35 (d, J=9 Hz, 1H), 6.89 (d, J=9 Hz, 1H), 6.85 (d, J=9 Hz, 2H), 6.65 (s, 1H), 4.10 (bs, 2H), 3.01 (s, 6H); $^{13}$C (DMSO-d$_6$) δ 178, 164, 151, 134, 129, 119, 118, 116, 114, 113, 108, 103, 39.5; ESI-MS: calculated molecular weight: 297 g; found: m/z 298.1 [(M+H)$^+$].

Example 10

Additional Compounds

Additionally the following compounds were prepared and characterized as follows:

2-(4-fluorophenyl)-7,8-dihydroxyquinolin-4(1H)-one.HBr (see structure 2 in FIG. 26): $^1$H NMR (300 MHz, DMSO-d$^6$) δ 10.83 (br s, 1H), 10.09 (br s, 1H), 7.92 (q, J1=5.1, J2=8.1 2H), 7.70 (d, J=8.7, 1H), 7.46 (t, J=8.7, 2H), 7.30 (d, J=9, 1H), 6.87 (s, 1H)$^+$, MS-ESI: cal. 271; found: 272 (M+H)$^+$. Anal. For C$_{15}$H$_{10}$FNO$_3$. 0.87HBr.2.4H$_2$O; calcd: C, 46.81; H, 4.10; N, 3.64; Br, 18.06; Found: C, 46.75; H, 3.80; N, 3.26; Br, 17.46; m.p.>300.

7,8-dihydroxy-2-phenylquinolin-4(1H)-one.HBr (see structure 3 in FIG. 26): $^1$H NMR (300 MHz, DMSO-d$^6$) δ 10.71 (br s, 1H), 7.81 (d, J=7.2, 2H), 7.65 (d, J=9.3, 1H), 7.57-7.66 (m, 3H), 7.23 (d, J=9.3, 1H), 6.81 (s, 1H), MS-ESI(negative): cal. 253; found: 252 (M−1). Anal. For C$_{15}$H$_{11}$NO$_3$. 0.8HBr.0.96H$_2$O; calcd: C, 53.74; H, 4.12; N, 4.18; Br, 18.90; Found: C, 53.45; H, 3.96; N, 4.43; Br, 19.11; m.p.: 269.8-274.2° C.

7,8-dihydroxy-2-(pyrimidin-5-yl)-4H-chromen-4-one.HBr (see structure 4 in FIG. 26): $^1$H NMR (300 MHz, CDCl$_3$) δ 10.27 (brs, 1H), 9.65 (brs, 1H), 9.52 (s, 2H), 9.32 (s, 1H), 7.39 (d, J=8.7, 1H), 7.10 (s, 1H), 6.94 (d, J=8.7, 1H); cal. 256; found: 257 (M+H)$^+$. Anal. for C$_{13}$H$_8$N$_2$O$_4$. 0.45H$_2$O. 0.3HBr; calcd: C, 54.10; H, 3.21; N, 9.71; Br, 8.31; Found: C: 54.30; H, 3.39; N, 9.41; Br, 8.37. m.p.>300° C.

Example 11

Figure 27:
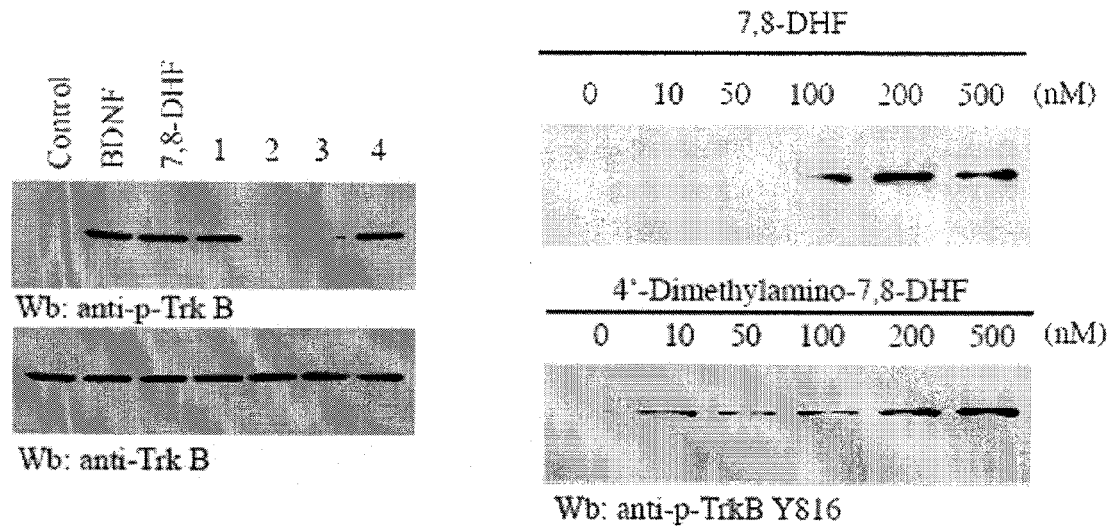
FIG. 27 shows Western blots illustrating the TrkB activation of the compounds from FIG. 26 (left panel) and Western blots illustrating in a titration assay illustrating the concentrations of 7,8-dihydroxyflavone and 4'-dimethylamino-7,8-dihydroxyflavone needed for TrkB activation (right panel).

4'-dimethylamino-7,8-dihydroxyflavone Displays Stimulatory Effect on TrkB Receptor To compare the TrkB activation by the synthetic compounds of Examples 9 and 10 (see FIG. 26), primary cortical cultures were prepared. The cortical neurons were treated with 500 nM of various compounds for 30 min and collected the cell lysates. Immunoblotting analysis (p-TrkB Y817 antibody (1:20,000-40,000 dilution)) revealed that 4'-dimethylamino-7,8-dihydroxyflavone ("4'-DMA-7,8-DHF") (see structure 1 of FIG. 26) and 7,8-dihydroxy-2(pyrimidin-5-yl)-4H-chromen-4-one (see structure 4 of FIG. 26) robustly provoked TrkB activation as positive control BDNF and 7,8-dihydroxyflavone ("7,8-DHF"), whereas 2-(4-fluoro-phenyl)-7,8-dihydroxyquinolin-4(1H)-one (see structure 2 of FIG. 26) and 7,8-dihydroxy-2-phenylquinolin-4 (1H)-one (see structure 3 of FIG. 26) did not provoke the same level of TrkB activation (FIG. 27, left panel). These data suggest that the O atom in the middle C ring increases 7,8-DHF's agonistic effect. Replacing the H-bond acceptor O atom with hydrogen bond donor NH reduced its stimulatory effect. Titration assay demonstrates that 4'-DMA-7, 8-DHF triggered TrkB activation at a concentration as low as 10 nM, and TrkB activity gradually increased as drug concentration escalated (see FIG. 27, right panels). In comparison, 7,8-DHF provoked TrkB activation with the minimal concentration of 100 nM (FIG. 27, right panels).

Figure 28:
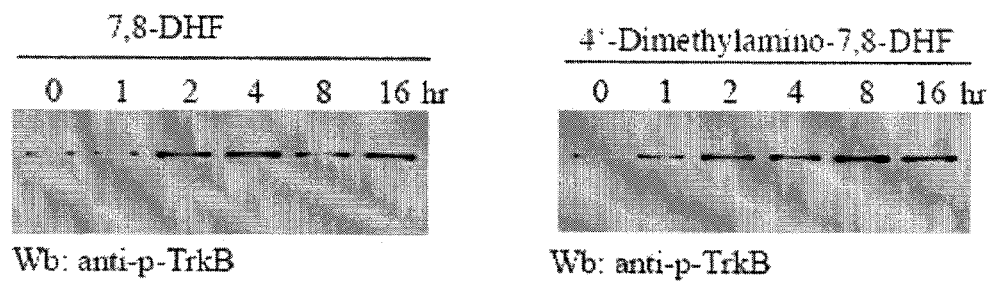
FIG. 28 shows Western blots illustrating the stimulatory effect of 7,8-dihydroxyflavone and 4'-dimethylamino-7,8-dihydroxyflavone on TrkB receptor in mouse brain.

To compare the stimulatory effect on TrkB receptor in mouse brain, 1 mg/kg of these compounds was injected into C57BL/6J mice and monitored TrkB activation at different time points (see FIG. 28). 4'-DMA-7,8-DHF elicited TrkB activation at 1 h and the activity of TrkB gradually escalated with the time and peaked at 8 h and partially decayed at 16 h. In contrast, 7,8-DHF triggered TrkB activation 2 h after oral injection and peaked at 4 h and TrkB activity progressively faded away. The TrkB activity was demonstrable even at 16 h (FIG. 28). As shown, 4'-DMA-7,8-DHF possesses a greater (i.e., about 10-fold higher) agonistic effect on TrkB than 7,8-DHF and its agonistic effect sustained longer in animals as well.

Example 12

4'-dimethylamino-7,8-dihydroxyflavone Possesses Robust Anti-apoptotic Activity

Figure 29:
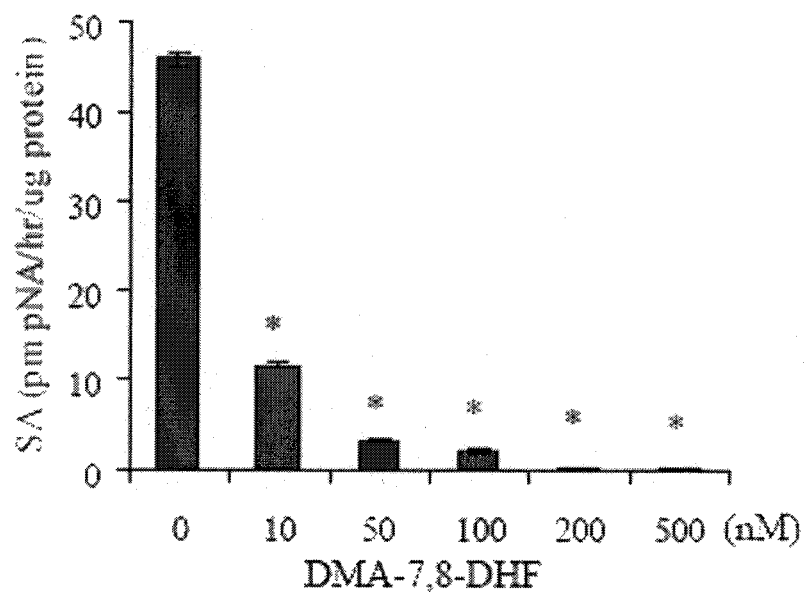
FIG. 29 shows bar graphs illustrating anti-apoptotic activity of 4'-dimethylamino-7,8-dihydroxyflavone (A) and 7,8-dihydroxyflavone (B) in cortical neurons.
Figure 29:
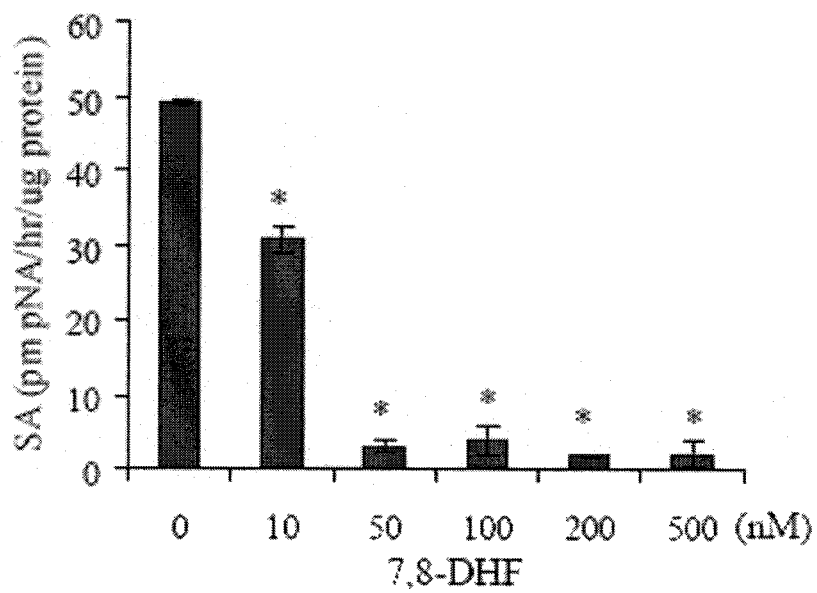

To quantitatively compare the anti-apoptotic activity of 7,8-DHF and 4'-DMA-7,8-DHF, cortical neurons were prepared from E16 rat embryonic cells and pretreated with various indicated concentrations of 4'-DMA-7,8-DHF and 7,8-DHF for 30 min, followed by 50 μM glutamate for 16 hours. The cell lysates were quantitatively analyzed with an active caspse-3 ELISA. Glutamate-provoked caspase-3 activation was substantially blocked by both compounds at 50 nM or higher concentrations. However, at 10 nM, 4'-DMA-7,8-DHF displayed a more robust inhibitory effect than 7,8-DHF (FIGS. 29A & 29B). These results fit with the TrkB receptor activation status by 4'-DMA-7,8-DHF and 7,8-DHF.

Figure 30:
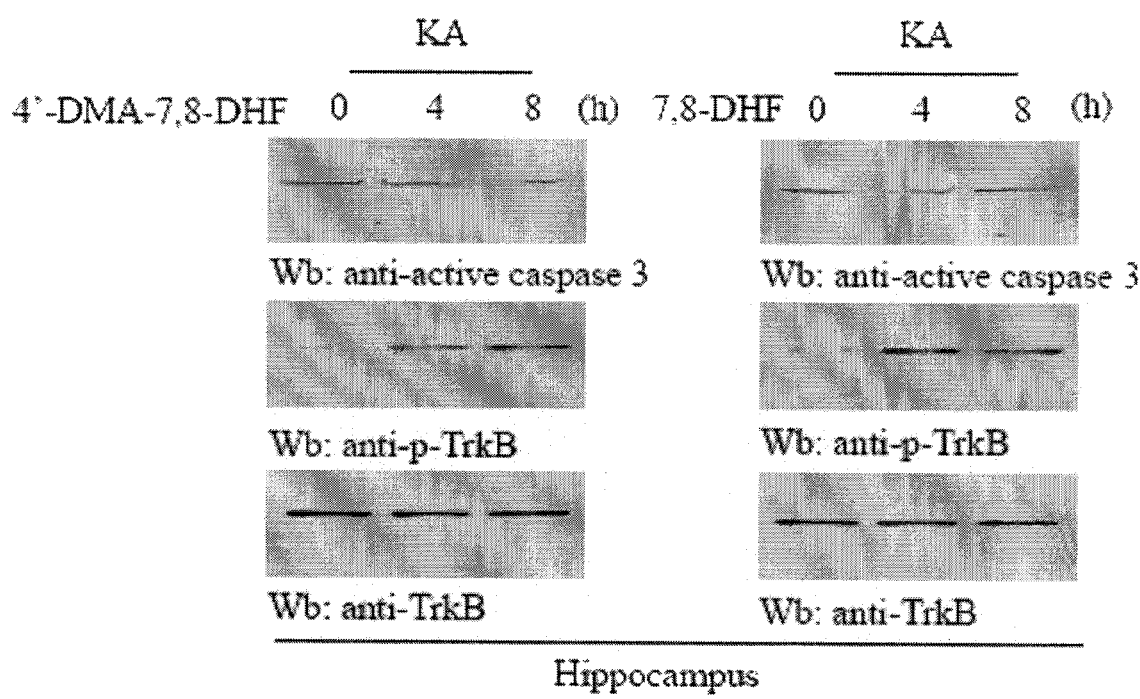
FIG. 30 shows Western blots illustrating the neuroprotective effect of 4'-dimethylamino-7,8-dihydroxyflavone (left panel) and 7,8-dihydroxyflavone (right panel) against kainic acid (KA) in mice.

To investigate whether these compounds exert any neuroprotective effects in animals, a time course assay was conducted. Both compounds were orally injected (1 mg/kg into C57BL/6J mice, followed by i.p. administration of kainic acid (KA)(20 mg/kg) for 2 h. Immunoblotting with mouse brain lysates demonstrated that KA-induced neuronal apoptosis was gradually decreased with time lapse, which inversely correlated with TrkB activation by 4'-DMA-7,8-DHF (FIG. 30, left panels). Nonetheless, KA-induced caspase-3 activation was reduced by 7,8-DHF at 4 h, and active caspase-3 was slightly increased at 8 h. This kinetic spectrum tightly coupled to TrkB activation status by 7,8-DHF (FIG. 30, right panel).

Figure 31:
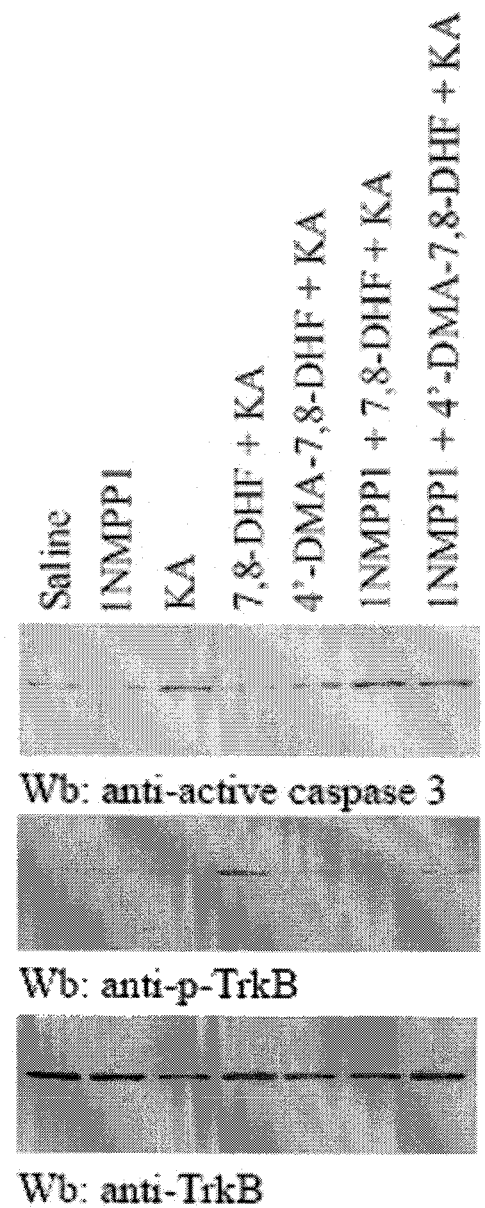
FIG. 31 shows Western blots further illustrating the neuroprotective effect of 4'-dimethylamino-7,8-dihydroxyflavone and 7,8-dihydroxyflavone against kainic acid (KA) in mice.

To explore whether the neuroprotective effect of these small molecules is dependent on TrkB activation in vivo, TrkB F616A knock-in mice were used. TrkB F616A can be selectively blocked by 1NMPP1, a TrkB F616A inhibitor, resulting in an effective TrkB-null phenotypes (Chen X, et al., Neuron 46(1):13-21, 2005. Because 1NMPP1 selectively inhibits TrkB F616A activation by 7,8-DHF, it was expected that blockade of TrkB F616A signaling by 1NMPP1 in TrkB F616A mutant knockin mice would make the neurons vulnerable to KA-provoked neuronal cell death. KA caused significant caspase-3 activation, which was markedly diminished by 4'-DMA-7,8-DHF and 7,8-DHF pretreatment. 1NMPP1 pretreatment abolished 4'-DMA-7, 8-DHF and 7,8-DHF's protective effect in F616A mice (FIG. 31, top panel). Accordingly, TrkB phosphorylation by 4'-DMA-7,8-DHF and 7,8-DHF was notably blocked by 1NMPP1 pretreatment (FIG. 31, $2^{nd}$ panel). Hence, these data demonstrate that 4'-DMA-7,8-DHF and 7,8-DHF selectively activate TrkB receptor and enhance neuronal survival in mice.

Example 13

4'-dimethylamino-7,8-dihydroxyflavone Promotes Neurogenesis

Figure 32:
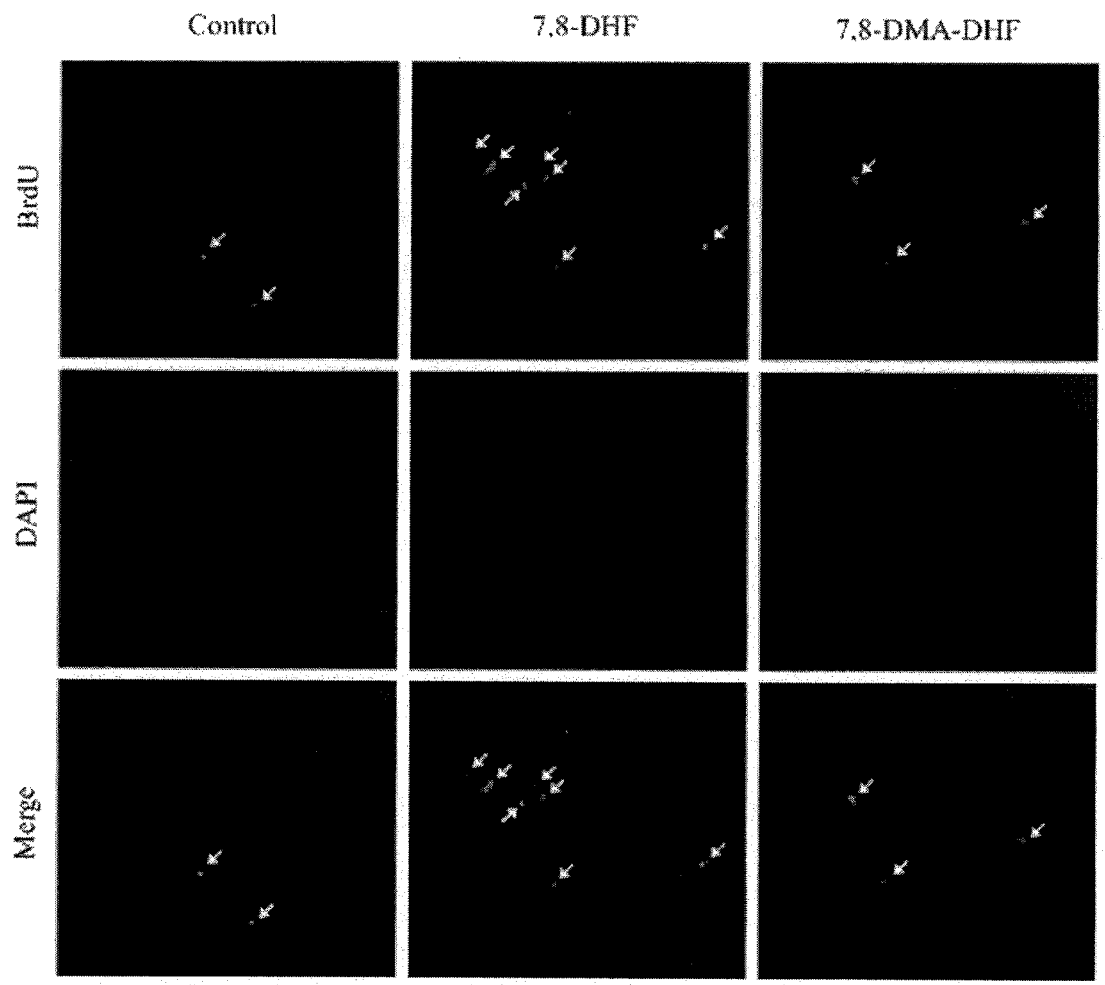
FIG. 32 shows BrdU immunofluorescent staining images showing increased neurogenesis for 7,8-dihydroxflavone and 4'-dimethylamino-7,8-dihydroxyflavone treated mice.
Figure 33:
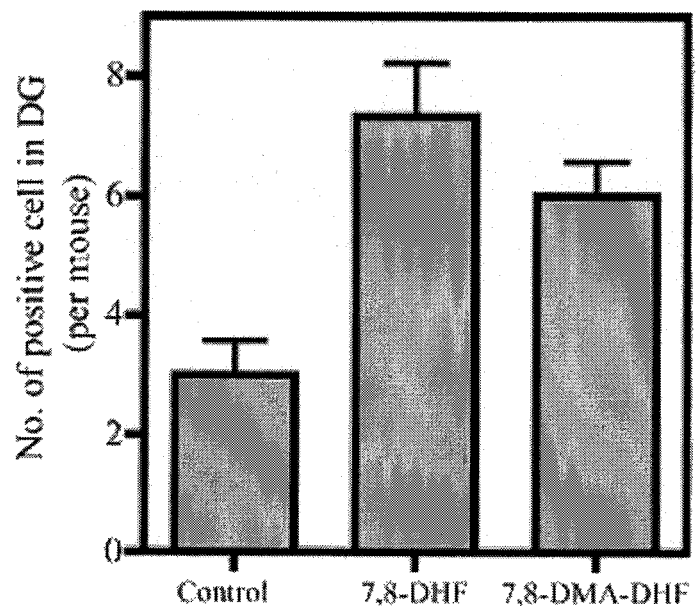
FIG. 33 shows a bar graph indicating the relative levels of neurogenesis shown in FIG. 32.

To test whether increasing TrkB activation by 4'-dimethylamino-7,8-dihydroxyflavone would elevate neurogenesis, adult male C57BL/6J mice were injected daily for 21 days with either vehicle, 7,8-DHF, or 4'-DMA-7,8-DHF (5 mg/kg). At the end of treatment (day 21), the animals were injected with BrdU (50 mg/kg, i.p.) to label the dividing cells and were sacrificed 2 hours later. Immunohistochemistry (anti-BrdU and DAPI) was used to assess progenitor proliferation (FIGS. 32 and 33). Long-term (21 days) TrkB agonists treatment were observed to significantly increased neurogenesis as compared to vehicle control. These results indicate that TrkB agonists promote neurogenesis in the hippocampus of mice.

Example 14

Figure 34:
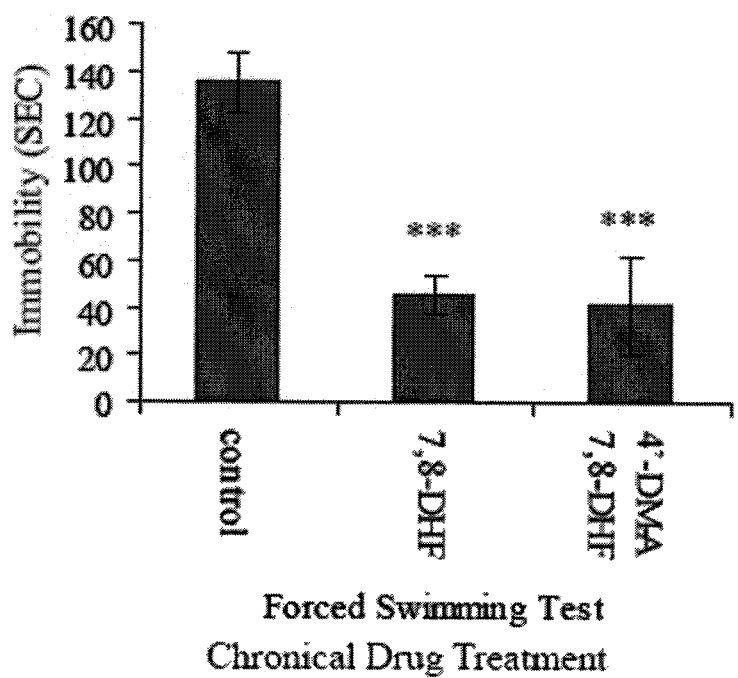
FIG. 34 shows a bar graph indicating increased mobility for 7,8-dihydroxflavone and 4'-dimethylamino-7,8-dihydroxyflavone treated mice in a forced swim test.
Figure 35:
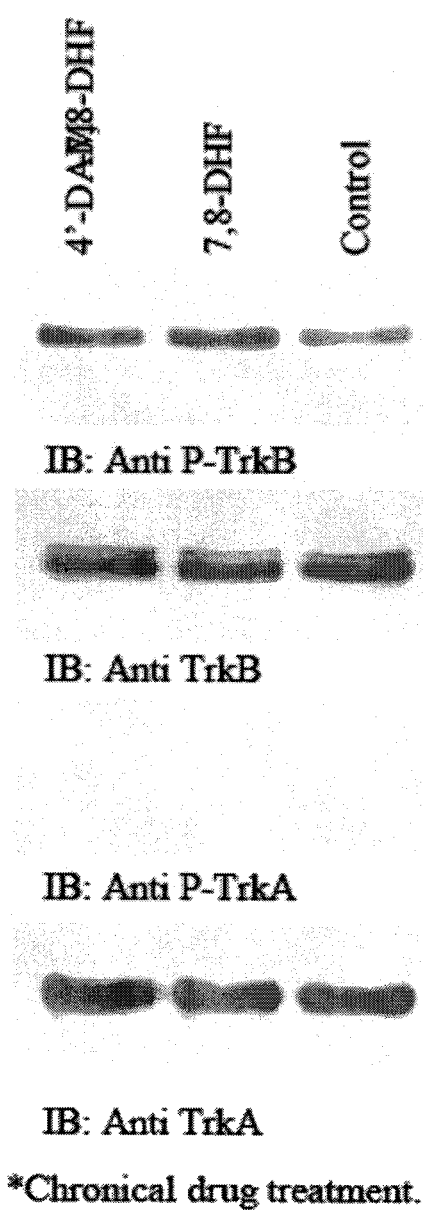
FIG. 35 shows Western blots of brain lysates from the mice used in the forced swim test of FIG. 34 indicating 7,8-dihydroxflavone and 4'-dimethylamino-7,8-dihydroxyflavone provoke TrkB but not TrkA activation in mouse brain.

4'-dimethylamino-7,8-dihydroxyflavone and 7,8-dihydroxyflavone Demonstrate Antidepressant Effect in a TrkB-dependent Manner To explore whether 4'-DMA-7,8-DHF and 7,8-DHF have any antidepressant effect, a forced swim test (6 minutes, immobility recorded in the last 4 minutes) was conducted after chronic treatment of male C57BL/6J mice (8 mice/group) for 21 days via oral injection. When mice were treated with 7,8-DHF (5 mg/kg), the swimming immobility was significantly decreased. Interestingly, 4'-DMA-7,8-DHF (5 mg/kg) also evidently reduced the immobility (FIG. 34), suggesting that 7,8-DHF and 4'-DMA-7,8-DHF imitate BDNF and exert a potent anti-depressant effect. Immunoblotting analysis (anti-p-TrkA 794 and anti-p-TrkB 817) using brain lysates from the forced swim test mice revealed that both compounds provoked TrkB but not TrkA activation in mouse brain (FIG. 35)

Figure 36:
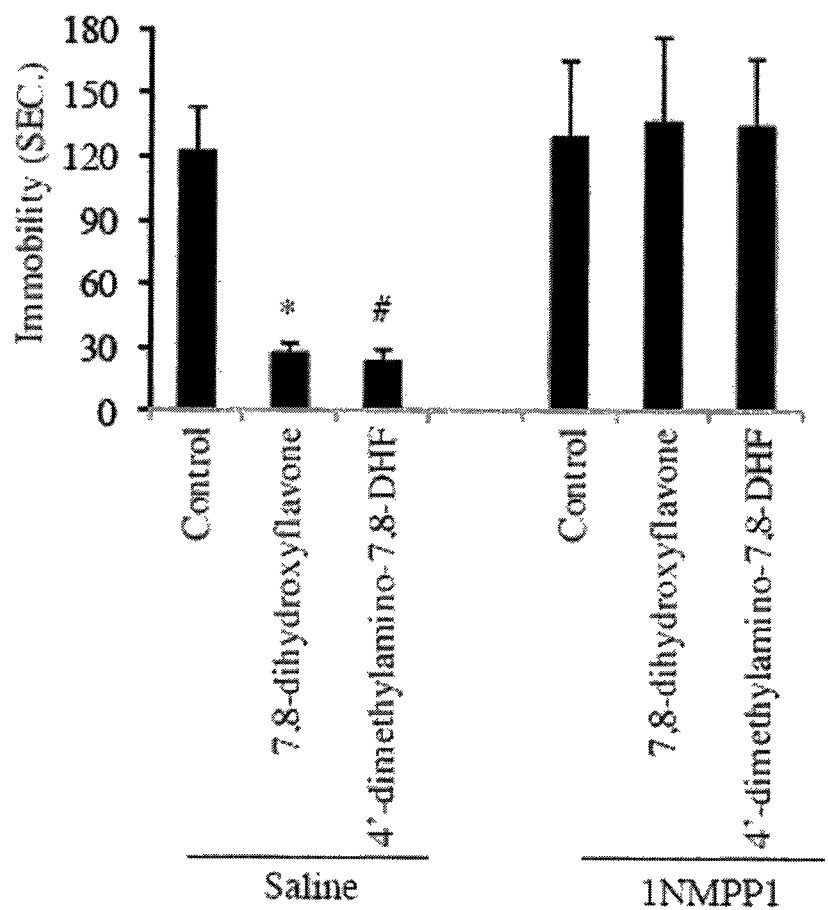
FIG. 36 shows a bar graph indicating increased mobility for 7,8-dihydroxflavone and 4'-dimethylamino-7,8-dihydroxyflavone treated mice in the saline group, but no significant different for mice pretreated with 1NMPP1.

To assess whether the behavior responses by 7,8-DHF and its derivative are mediated by TrkB receptor, TrkB F616A knockin mice were utilized. The transgenic mice were subjected to saline or 1NMPP1 pretreatment (25 µM), respectively (drinking water provided one day prior to drug injection and maintained throughout whole experiment). The control and/or drugs were provided for five days. No significant difference was observed in the immobility time between saline and 1NMPP1 treated control groups. In the saline group, both 7,8-DHF and 4'-DMA-7,8-DHF substantially reduced the immobility time; in contrast, neither 4'-DMA-7,8-DHF nor 7,8-DHF had any significant effect on the immobility time after 1NMPP1 treatment (FIG. 36), showing that inhibition of TrkB signaling cascade blocks the antidepressant effect by the TrkB agonists. These data demonstrated that 4'-DMA-7,8-DHF and 7,8-DHF mimic BDNF and act as potent antidepressant drugs in mice through activating the TrkB receptor. (Data presented in FIGS. 34, 35, and 36 as mean±SEM; *$p<0.05$ against vehicle, #$P<0.01$ against vehicle and ***$P<0.0001$ against vehicle, student t-test.)

Example 15

4'-dimethylamino-7,8-dihydroxyflavone and 7,8-dihydroxyflavone Toxicity

To explore whether 4'-dimethylamino-7,8-dihydroxyflavone and 7,8-dihydroxyflavone have any intolerable toxicity, the major organs from mice treated with both compounds at 5 mg/kg/day for 3 weeks were analyzed. No appreciable adverse pathological change was detected in the drug-treated mice. In addition, a complete blood count (CBC) analysis showed that there was no significant difference between the drugs-treated mice and control saline-treated mice. These data showed that neither compound was toxic to the mice at 5 mg/kg/day dose for 3-week chronic treatment.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus a combination of steps, elements, components, or constituents may be explicitly mentioned herein; however, all other combinations of steps, elements, components, and constituents are included, even though not explicitly stated.

What is claimed is:

1. A method of treating depression comprising:
    administering a therapeutically effective amount of 7,8-dihydroxyflavone to a subject in need thereof.
2. The method of claim 1, wherein 7,8-dihydroxyflavone is administered orally.
3. The method of claim 1, wherein 7,8-dihydroxyflavone is administered by injection.

* * * * *